US009901543B2

United States Patent
Chausson et al.

(10) Patent No.: US 9,901,543 B2
(45) Date of Patent: Feb. 27, 2018

(54) THERMOGELLING COMPOSITION

(71) Applicant: KiOmed Pharma, Herstal (BE)

(72) Inventors: Mickaël Chausson, Wanze (BE); Renaud Lecler, Ougree (BE)

(73) Assignee: KIomed Pharma, Herstal (BE)

( * ) Notice: Subject to any disclaimer, the term of this patent is extended or adjusted under 35 U.S.C. 154(b) by 0 days.

(21) Appl. No.: 15/420,462

(22) Filed: Jan. 31, 2017

(65) Prior Publication Data

US 2017/0135952 A1 May 18, 2017

Related U.S. Application Data

(63) Continuation-in-part of application No. PCT/EP2015/067754, filed on Jul. 31, 2015.

(30) Foreign Application Priority Data

Aug. 1, 2014 (FR) ..................................... 14 57547

(51) Int. Cl.
| | | |
|---|---|---|
| A01N 43/04 | (2006.01) | |
| A61K 9/00 | (2006.01) | |
| A61K 47/26 | (2006.01) | |
| A61K 9/06 | (2006.01) | |
| A61L 27/20 | (2006.01) | |

(52) U.S. Cl.
CPC .............. A61K 9/0024 (2013.01); A61K 9/06 (2013.01); A61K 47/26 (2013.01); A61L 27/20 (2013.01); *A61L 2400/06* (2013.01)

(58) Field of Classification Search
CPC .................................................. A61K 31/722
USPC .......................................................... 514/55
See application file for complete search history.

(56) References Cited

U.S. PATENT DOCUMENTS

2013/0244972 A1    9/2013   Ben-Shalom et al.

OTHER PUBLICATIONS

Chang et al., "Preparation and Properties of a Novel Thermosensitive N-Trimethyl Chitosan Hydrogel", Polymer Bulletin, 2009, pp. 531-545, vol. 63.
English Translation of the International Search Report for PCT/EP2015/067754 dated Sep. 25, 2015.
English Translation of the International Search Report for PCT/EP2015/067755 dated Sep. 25, 2015.
Hsiao et al., "Design and Characterization of a Novel Amphiphilic Chitosan Nanocapsule-Based Thermo-Gelling Biogel with Sustained In Vivo Release of the Hydrophilic Anti-Epilepsy Drug Ethosuximide", Journal of Controlled Release, 2012, pp. 942-948, vol. 161.
Hsiao et al., "Supplementary Material for Design and Characterization of a Novel Amphiphilic Chitosan Nanocapsule-Based Thermo-Gelling Biogel with Sustained In Vivo Release of the Hydrophilic Anti-Epilepsy Drug Ethosuximide; Detailed Version of: 2.4. Morphological Characterization of CHC Nanogels", Journal of Controlled Release, 2012, vol. 161.
Jarry et al., "Irradiating or Autoclaving Chitosan/Polyol Solutions: Effect on Thermogelling Chitosan-β-Glycerophosphate Systems", 2002, Chemical and Pharmaceutical Bulletin, pp. 1335-1340, vol. 50, No. 10.
Ji et al., "Biocompatibility of a Chitosan-Based Injectable Thermosensitive Hydrogel and its Effects on Dog Periodontal Tissue Regeneration", Carbohydrate Polymers, 2010, pp. 1153-1160, vol. 82.
Ji et al., "Injectable Thermosensitive Hydrogel Based on Chitosan and Quatremized Chitozan and the Biomedical Properties", Journal of Material Science: Materials in Medicine, 2009, pp. 1603-1610, vol. 20.
Ji et al., "Sterilization-Free Chitosan Hydrogels for Controlled Drug Release", Materials Letters, 2012, pp. 110-112, vol. 72.
Khor et al., "Implantable Applications of Chitin and Chitosan", Biomaterials, 2003, pp. 2339-2349, vol. 24.
Written Opinion for PCT/EP2015/067754 dated Sep. 25, 2015.
Written Opinion for PCT/EP2015/067755 dated Sep. 25, 2015.
Wu et al., "A Thermo- and pH-Sensitive Hydrogel Composed of Quatemized Chitosan/Glycerophosphate" International Journal of Pharmaceuticals, 2006, pp. 1-11, vol. 315.
Zang et al., "A Comparison of Physicochemical Properties of Sterilized Chitosan Hydrogel and its Applicability in a Canine Model of Periodontal Regeneration", Carbohydrate Polymers, 2014, pp. 240-248, vol. 113.
Borrell et al., "Lift Capabilities of Hyaluronic Acid Fillers", Journal of Cosmetic and Laser Therapy, 2011, pp. 21-27, vol. 13.
Bourdon et al., "Lift Capabilities evaluation of Hyaluronic Acid fillers", Poster presentation AMWC Monaco 2012.
Gao et al., "PLGA-PEG-PLGA Hydrogel for Ocular Drug Delivery of Dexamethasone Acetate," Drug Development and Industrial Pharmacy, 2010, pp. 1131-1138, vol. 36, No. 10.
Zhang et al, "Sustained Intravitreal Delivery of Dexamethasone Using an Injectable and Biodegradable Thermogel", Acta Biomaterialia, 2015, pp. 271-281, vol. 23.

*Primary Examiner* — Raymond J Henley, III
(74) *Attorney, Agent, or Firm* — Thompson Coburn LLP; William A. Holtz

(57) ABSTRACT

The invention relates to a thermogelling composition comprising a chitosan having N-acetyl-glucosamine units, glucosamine units, and substituted glucosamine units other than the N-acetyl-glucosamine units, said substituted chitosan preferably having a degree of substitution of the glucosamine units ranging from 10 to 50%, expressed as a number of moles of the substituent based on the number of moles of total units, to its preparation and to its applications.

35 Claims, 1 Drawing Sheet

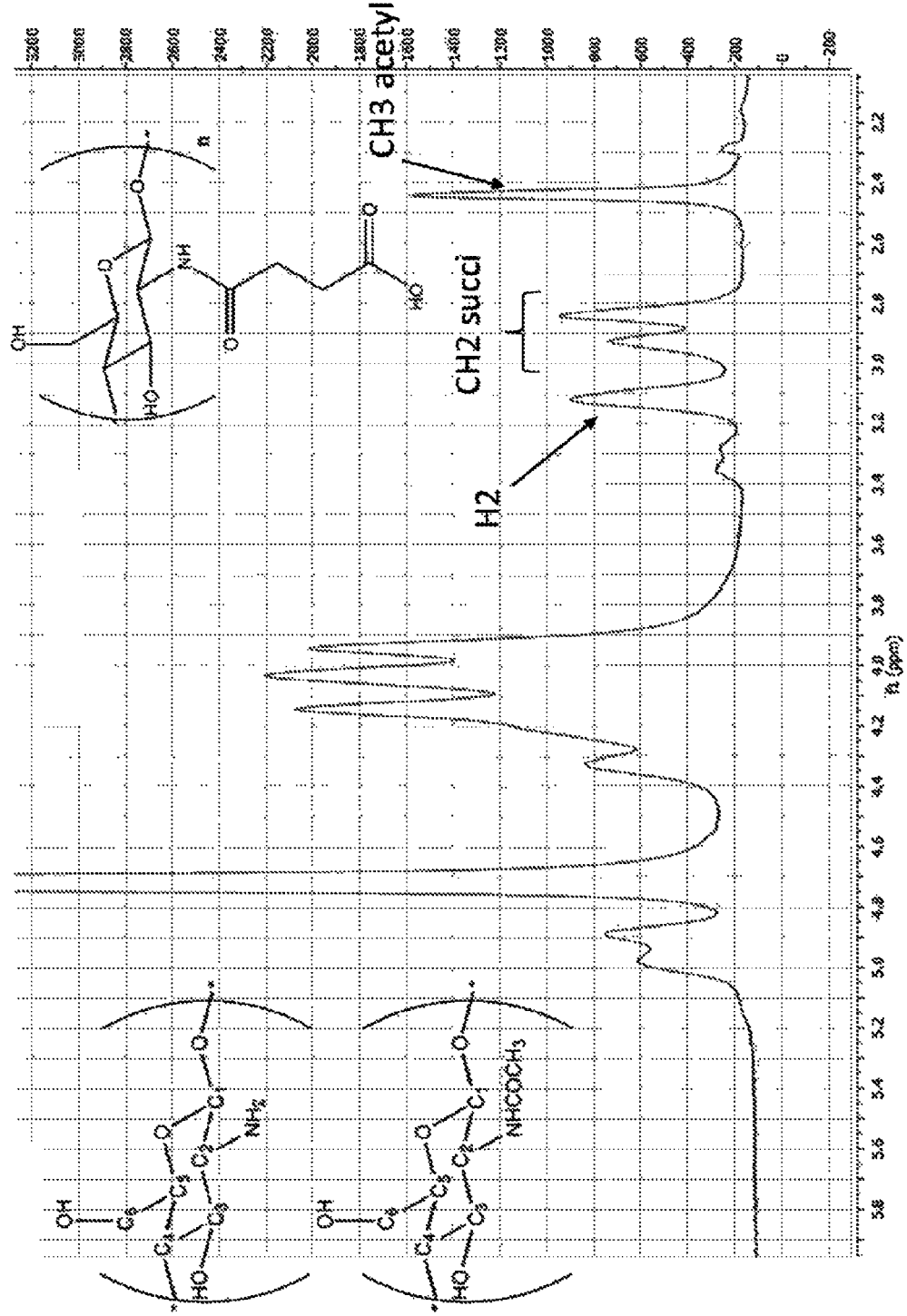

THERMOGELLING COMPOSITION

CROSS-REFERENCE TO RELATED APPLICATIONS

This application is a continuation-in-part application of the international patent application PCT/EP2015/067754 filed on Jul. 31, 2015, claiming the priority of the French patent application 14 57547 filed on Aug. 1, 2014, both of which are incorporated by reference herein in their entireties.

The present invention relates to a thermogelling composition. This composition is notably adapted to its injection into a human or animal being, more particularly into a human being. The present invention also relates to a therapeutic prevention or treatment method and to an esthetical care method notably comprising the injection of a thermogelling composition of the invention.

Injection of compositions based on biopolymers, e.g. hyaluronic acid because of its viscoelastic properties, for example for a therapeutic treatment, is quite well-known. This type of composition is notably useful in the treatment of articular pain, in particular from arthrosis. These compositions are also known for achieving the filling of tissue, such as the dermis. This filling may occur for an estheical purpose or within the scope of reparatory surgery treatment.

The use of compositions based on chitosan as a biopolymer is also known for tissue repair, in particular for repairing defects of the cartilage liwed with blood. Preparation and use of chitosan-based solutions associated with agents that cause a sol-gel transition of the solution at a physiological temperature are also known for injection into tissues and joints.

Such compositions may be used for example in an intra-tissular injection (e.g. subcutaneous, intradermal injection), intra-articular or intra-ocular injection. This may be for protecting or repairing a joint which exhibits signs of arthrosis or lesion of the cartilage by injecting a viscous fluid. This may further be for filling a tissue or an organ for promoting its repair or for increasing the volume thereof.

For providing such compositions, The technical problem generally occurs of being able to provide a composition, for which the physico-chemical properties are close to those of the tissues or fluids of the injection area. However, the problem of injecting such a viscous fluid is posed, since when it has physico-chemical properties close to the desired ones, for example in terms of viscosity, these compositions are very difficult to inject, or even impossible to inject.

Along the sought solutions, mention may notably be made of American U.S. Pat. No. 6,344,488 which teaches the preparation of a thermogelling composition comprising chitosan. This composition is also highly sensitive to the pH, and may, according to the value of the pH, either have reversibility of the sol-gel transition or not. Reversibility of the sol-gel transition is important since it allows sterilization by raising the temperature. The composition also comprises glycerol phosphate at a rather high concentration. It is however noted that according to Table 2 of this patent, the chitosan at a concentration below 1.5% (mass/volume) is not gelled at 37° C. Now, this is the average body temperature of a non-feverish human being. The compositions used have a concentration of 2% (m/v). It is advantageous to provide a composition comprising chitosan in a concentration which may be lower. The compositions described in this patent have a pH of at most 7.05. It is therefore advantageous to provide a composition comprising chitosan having a pH closer to the physiologica pH for the targeted applications.

Moreover, the thermogel described in this patent does not seem to be able to be sterilized with steam. This is therefore a major drawback.

Therefore, the need exists for providing a thermogelling composition, gelled at a physiological temperature of a human being, having good viscoelastic properties for therapeutic or esthetical applications.

Moreover, the compositions of gels, in particular hydrogels, either thermogelling or not, may not have an osmolality of less than 750 mosmol/kg.

The invention has the purpose of solving these technical problems. The object of the invention is notably to provide a thermogelling composition which may easily be injected while being gelled at a physiological temperature of a human being. Such a composition should have good physico-chemical properties for therapeutic or esthetical applications, in particular at the physiological temperature of the human or animal body, for example 37° C. for uses after implantation. More particularly, such a composition should be able to have physico-chemical properties which may be modulated depending on the aimed application so as to be as close as possible to the required properties for the targeted therapeutic or esthetical purpose.

The object of the invention is also to provide a thermogelling composition for which the pH is acceptable for the targeted therapeutic or esthetical applications. More particularly, such compositions should be able to have a pH which may be modulated depending on the targeted application, notably so as to be as close as possible to the physiological pH.

The object of the present invention is also to provide a thermogelling composition for which the osmolality is controlled and for example close to the physiological one for the targeted therapeutic or esthetical application, in particular an osmolality ranging from 100 to 700 mosm/kg, and in particular from 200 to 500 mosm/kg (also written as <<mosmol/kg>>).

The object of the present invention is also to provide a composition for which the sol-gel transition is reversible, notably in order that the storage and/or transport conditions do not require drastic control of the temperature, and/or that the composition may undergo sterilization by a rise in temperature.

The object of the present invention is also to provide a composition for which the cohesion of the gel promotes storage and/or transport without requiring drastic control of the temperature, and/or that the composition may be subject to sterilization by a rise in temperature.

According to an alternative, the object of the invention is also to provide a composition for which the biopolymer and more specifically chitosan content is low. Such a content should be less than 5%, preferably less than 2%, by mass of chitosan based on the total mass of the composition The object of the invention is further to provide a composition which may be used as a viscosupplement, and in particular being able to be injected into or mixed with a synovial fluid. The object of the invention is notably to provide a reconstructed synovial fluid, i.e. a composition restoring the properties of a joint, in particular by providing it with a capability of absorbing shocks during a movement and of being lubricated at least at rest.

The object of the invention is further to provide a composition having good properties in a mixture with a synovial fluid and in particular a synovial fluid of a human being. Advantageously, the object of the invention is to provide a composition having good resistance to degradation in an inflammatory environment, in particular in terms of conservation of the elastic modulus G' and of the viscosity at rest.

The present invention surprisingly allows one or several problems mentioned above to be solved.

It was surprisingly discovered that such a thermogelling composition may be prepared when this composition comprises a chitosan having N-acetyl-glucosamine units, glucosamine units, and substituted glucosamine units other than N-acetyl-glucosamine units, said substituted chitosan preferably having a degree of substitution of the glucosamine units ranging from 10 to 50%, expressed as a number of moles of the substituent relatively to the number of moles of total units.

According to a particular embodiment, the glucosamine units are D-glucosamine units (D-glucosamine units, substituted D-glucosamine units, N-acetyl-D-glucosamine units and optionally substituted N-acetyl-D-glucosamine units).

According to an alternative, the chitosan has N-acetyl-D-glucosamine units, D-glucosamine units, and substituted D-glucosamine units other than N-acetyl-D-glucosamine units, and optionally substituted N-acetyl-D-glucosamine units.

By <<substituted D-glucosamine units other than N-acetyl-D-glucosamine units>>, is meant that the substituted D-glucosamine units do not form N-acetyl-D-glucosamine units after substitution.

According to an alternative, a substituted chitosan has only a substitution of the D-glucosamine units.

According to another alternative, a substituted chitosan has a substitution of D-glucosamine and N-acetyl-D-glucosamine units simultaneously, and wherein the substitution group is bound covalently, according to an alternative to only the amine groups of the chitosan, or according to another alternative to the amine and hydroxyl groups of the chitosan simultaneously.

According to an embodiment, the degree of substitution of the D-glucosamine units expressed as a number of moles of D-glucosamine units relatively to the number of moles of total units (D-glucosamine and N-acetyl-D-glucosamine units, either substituted or not) of the substituted chitosan, ranges from 0.1 to 0.5%.

It was discovered according to a specific alternative, that a degree of substitution of the glucosamine units, expressed as a number of moles of glucosamine units on which the substituting group is attached through a covalent bond, relatively to the number of total moles of glucosamine and N-acetyl-glucosamine units of the substituted chitosan, from 0.1 to 0.5 advantageously allow solubilization of the substituted chitosan, optionally in the presence of a gelling agent, for example a polyol or sugar salt, and more particularly a glycerol phosphate salt, at a pH and at a temperature in a range particularly adapted to the targeted applications. It may be more simple to express the degree of substitution by the molar ratio or by the mass ratio of the starting reagents with respect to the chitosan, as explained later on.

According to an alternative, the substituted chitosan is soluble because of its degree of substitution in a water solution buffered to pH 7, for example with a phosphate salt buffer (PBS), the solution comprising a 1% by mass substituted chitosan concentration with respect to the mass of the total solution, the pH being measured at 8° C.

According to an alternative, notably when the substituted chitosan has a zwitterionic nature, there exists a narrow pH range in which the substituted chitosan is not soluble. This particularity is circumvented according to prior art by adding a gelling agent, for example a polyol or sugar salt, and more particularly a glycerol phosphate salt, so that the substituted chitosan is solubilized at the relevant pH of interest for the invention.

By substituting the chitosan, it was possible to prepare a solution of a soluble substituted chitosan in an aqueous solution for which the pH varies in a wide range, while non-substituted chitosan is only soluble at a pH below 5.5 to 6.5. The aqueous solution of substituted chitosan may generally have a pH ranging from 6.5 to 8.5. This solution according to the invention may be gelled. The sol-gel transition or gelling may therefore be achieved at neutral pH or at a physiological pH, such as for example a pH comprised between 7 and 8.5, while chitosan is not soluble at pH 7, the pKa of the amine groups being of about 5.5 (and therefore not charged at pH 7 at which the amine groups are not protonated). The substituted chitosan thus has a capability of being solubilized at different pHs by means of the presence of substituting groups which modify its solubilization profile. Surprisingly, it was possible to prepare thermogelling compositions with a substituted chitosan, and in particular with a low concentration of chitosan, in particular with a chitosan of very low, low or average molecular mass, while having a reversible sol-gel transition. Such a composition comprising a substituted chitosan has a sol-gel transition when the temperature increases. Thus, in a very advantageous way, the sol-gel transition, i.e. the passing from the solution in the fluid state to the gel state, may be modulated depending on the degree of substitution so that this sol-gel transition notably occurs under desired conditions of pH, osmolality and temperature.

The invention therefore advantageously according to an alternative allows preparation of a fluid themogelling composition at a temperature of less than the one of use, typically at a temperature less than the physiological temperature, for example 37° C., but which is as a gel at the temperature of use, typically at the physiological temperature, for example 37° C., at a neutral pH (pH 7) or at a physiological pH, and for example from 7 to 8.5, with a suitable osmolality for the contemplated use. This is for example a physiological osmolality.

According to another alternative, the invention relates to a thermogelling composition, as a gel before use, typically at room temperature, and for example at a storage temperature (for example from 4 to 8° C.), and at a temperature of use, typically at the physiological temperature, for example 37° C., at neutral pH (pH 7) or at a physiological pH, and for example from 7 to 8.5, with an osmolality suitable for the contemplated use. This is for example a physiological osmolality.

By <<thermogelling composition>> or <<thermogel>> is meant a fluid, and notably a solution which has the property of undergoing a sol-gel transition by modification of the temperature, preferably by increasing the temperature, and still preferably by increasing the temperature up to the physiological temperature of the human or animal body, and thus appearing as a gel at the physiological temperature after injection or implantation. The thermogelling composition of the invention may appear as a hydrogel, i.e. an aqueous gel.

According to the present invention, by gel is meant a composition which does not flow under its own weight, and more specifically not exhibiting any flow in the absence of external stimuli by turning upside down a container containing the composition for example for 30 seconds, and characterized by an elastic modulus G' greater than the loss modulus G", the moduli being measured by rheology by means of a rheometer with <<Couette>> geometry or by means of a rheometer with planar geometry and with sweeping in an low amplitude oscillatory mode (for example the rheometer <<Discovery Hybrid DHR-2>> (TA Instruments)). The difference between the moduli G' and G" of the gel are the characteristic of the cohesion of the gel.

According to the present invention, by <<fluid>> is meant a composition which flows under its own weight upon turning upside down a container containing the composition for example for 30 seconds and characterized by an elastic modulus G' less than the loss modulus G", the moduli being measured by rheology by means of a rotary rheometer with Couette shearing (shearing of the fluid between two coaxial cylinders).

Advantageously, it was discovered that the degree of substitution of the D-glucosamine units gives the possibility of modulating the sol-gel transition. Thus the invention advantageously gives the possibility of providing a thermogelling composition in which the minimum degree of substitution of the chitosan is selected so that the substituted chitosan is soluble in the thermogelling composition. It is also possible to check the solubility in different buffers. By <<soluble in water>>, is meant that the substituted chitosan does not have any turbidity visible to the naked eye. More specifically, it is possible to confirm the lack of turbidity for an optical density of less than 0.5, and preferably less than 0.2, as measured by UV-visible spectrometry at the wavelength of 600 nm of a sample comprising water optionally buffered with a buffer of the relevant pH, for example like sodium acetate at 0.5M, with reference to a reference tank only comprising the aqueous solvent used for the measured sample, but in the absence of the substituted chitosan. When the chitosan is not sufficiently substituted, the composition is not soluble in a satisfactory pH range, for example ranging from pH=7 to pH=8.5, at room temperature, and therefore is not either capable of thermogelling when the temperature is increased.

The invention gives the possibility of providing a thermogelling composition in which the maximum degree of substitution of the chitosan is selected so that a sol-gel transition is carried out at a temperature below the temperature of use, preferably below the physiological temperature, for example the temperature of 37° C. The sol-gel transition may be ascertained by the crossover of the moduli G' and G" according to the method defined in the invention.

Advantageously, the degree of substitution is determined by nuclear magnetic resonance spectrometry (NMR) of the proton in solution in an aqueous medium, by means of a magnetic resonance spectrometer, for example a Bruker spectrometer of frequency 400 MHz. The samples are prepared in the following way: 5 to 6 mg of substituted chitosan are dissolved in 1 ml of deuterated water. 2 µl of deuterated hydrochloric acid of concentration 12M are added to the solution of substituted chitosan in order to attain a suitable pH zone for the analysis. The suitable pH zone depends on the nature of the substituent. The spectrum is recorded at a temperature of 70° C., with a number of scans ranging from 64 to 256 and a relaxation time ranging from 1 to 8 seconds. The obtained spectrum is treated by deconvolution in order to determine the value of the integral of the areas of the signals of interest so as to be able to calculate the degree of substitution of the substituted chitosan.

The method for preparing the sample, the conditions for recording the NMR spectrum, and the formula used for calculating the degree of substitution have to be adapted to each type of substituted chitosan, since they depend on the nature and on the position of the substituent.

An example of the calculation of the degree of substitution (DS) is given below for the case of chitosan substituted with a succinyl group bound to the amine group of the D-glucosamine units (chitosan succinamide, Formula 1). The abbreviations are the following: $I_{H2}$ is equal to the integral of the area of the signal of the proton of the D-glucosamine units in position 2; $I_{CH2\ succi}$ is equal to the integral of the area of the signal of the protons of the two—CH2 groups of the succinyl substituent bound to the D-glucosamine units (on the carbon atoms in the alpha and beta position of the amide function); $I_{CH3\ acetyl}$ is equal to the integral of the area of the signal of the protons of the acetyl groups of the N-acetyl-D-glucosamine units.

An NMR spectrum example of chitosan succinamide and the structural formula of the chitosan succinamide are illustrated in FIG. 1.

$$\% \ DS = \frac{I_{CH2succi}/2}{I_{H2} + I_{CH2succi}/2 + I_{CH3acétyle}/3}$$

Formula 1-Calculation of the degree of substitution of the chitosan substituted with a succinyl group by proton NMR.

If another NMR method is more advantageous for estimating the degree of substitution in a reliable way, such a method should be used. The formula above should be adapted by one skilled in the art as regards the preparation of the sample and the signals to be integrated, notably depending on the resolution, on the robustness and on the position of the protons of the signals to be used for calculating the degree of substitution.

Advantageously, the composition has a thermoreversible sol-gel transition.

Advantageously, the present invention gives the possibility of providing a composition with a low concentration of substituted chitosan.

Advantageously, the chitosan concentration is less than 4%, for example less than 3%, or further for example less than 2% by mass based on the total mass of the composition (m/m).

According to a specific alternative, the concentration of substituted chitosan is less than 1.9% (m/m), expressed by mass based on the mass of the final composition. Advantageously, the concentration of substituted chitosan is comprised between 0.5 and 1.5% (m/m), expressed by mass based on the mass of the final composition. According to a particular alternative, the concentration of substituted chitosan is of about 1.2% (m/m), expressed by mass based on the mass of the final composition.

According to a particular alternative, the concentration of substituted chitosan is of about 2.5% (m/m), expressed by mass based on the mass of the final composition.

According to a particular embodiment, the concentration of substituted chitosan is of about 2.0% (m/m), expressed by mass based on the mass of the final composition.

According to a particular alternative, the concentration of substituted chitosan is of about 1.5% (m/m), expressed by mass based on the mass of the final composition.

According to a particular alternative, the concentration of substituted chitosan is of about 1.3% (m/m), expressed by mass based on the mass of the final composition.

According to a particular alternative, the concentration of substituted chitosan is of about 1.1% (m/m), expressed by mass based on the mass of the final composition.

According to a particular alternative, the concentration of substituted chitosan is of about 1.0% (m/m), expressed by mass based on the mass of the final composition.

According to a particular alternative, the concentration of substituted chitosan is of about 0.9% (m/m), expressed by mass based on the mass of the final composition.

Moreover, the degree of substitution of the D-glucosamine units advantageously gives the possibility of not using a solution with an acid pH (typically 5.0 to 5.5) for solubilizing the chitosan and of not having necessarily to add a sugar or polyol salt, like glycerol phosphate, to increase the pH up to about 7. On the contrary, the present invention advantageously gives the possibility of directly preparing a solution with a neutral pH or a physiological pH, such as for example from 6.2 to 8.5, in which the substituted chitosan is soluble and therefore also has the advantage for example of not having to necessarily need the addition of an acid solution for solubilizing the chitosan. This has the advantage of ensuring much more freedom on the range of pH which may be used for the thermogelling composition, and thus preparing thermogelling compositions at a neutral or physiological pH. For example it is possible to use a buffer agent which is an acid or a base for adjusting the pH. For example a basic buffer may be used and then the pH of the thermogelling composition may be adjusted with a weak acid.

According to an advantageous alternative, the thermogelling composition does not comprise any gelling agent. According to this alternative, the thermogelling composition has the property of gelling by the sole presence of the substituted chitosan. In particular, according to this alternative, the composition does not comprise a gelling agent as defined in the invention. In particular, according to a preferred alternative, the thermogelling composition of the invention does not comprise any glycerol salt, and in particular no glycerol phosphate salt (also written in the form of <<glycerophosphate>>). This alternative gives the possibility of avoiding the presence of glycerol phosphate or of any other equivalent gelling agent, the technical effect of which is only mechanical on the gel. According to this alternative, it is preferred to avoid the compounds like gelling agents which do not have any therapeutic benefit or any interaction of a biological/chemical nature with the body of the treated subject.

According to an alternative, the composition comprises a gelling agent, preferably a gelling agent inducing a sol-gel transition of the composition, for example a glycerol phosphate salt for example in the sodium or calcium form, for example in its pentahydrate form, said gelling agent being preferably present in the composition at a concentration comprised between 1 and 20%, preferably 3 and 9%, by mass based on the total mass of the final composition (m/m).

The gelling agent is advantageously at least one polyol or sugar salt, including any of their mixtures.

From among the polyol or sugar salts, mention may notably be made of phosphate salts, and more particularly dibasic polyol or sugar mono-phosphate salts. Mention may also be made of sulfate salts such as for example the polyol or sugar mono-sulfate salts. From among the phosphate salts, mention may notably be made of dibasic glycerol mono-phosphates, including glycerol-2-phosphate, sn-glycerol-3-phosphate and 1-glycerol-3-phosphate. According to an alternative, this is beta-glycerol phosphate. From among the polyols and sugars for such salts, mention may be made of the following polyols and sugars: histidinol, acetol, diethylstilbestrol, indoleglycerol, sorbitol, ribitol, xylitol, arabinitol, erythritol, inositol, mannitol, glucitol, palmitoyl-glycerol, linoleoyl-glycerol, oleoyl-glycerol, arachidonoyl-glycerol, fructose, galactose, ribose, glucose, xylose, rhamnulose, sorbose, erythrulose, deoxy-ribose, ketose, mannose, arabinose, fuculose, fructopyranose, ketoglucose, sedoheptulose, trehalose, tagatose, sucrose, allose, threose, xylulose, hexose, methylthio-ribose or methylthio-deoxy-ribulose, or any of their mixtures.

According to a specific alternative, the polyol or sugar salt concentration and preferably glycerol salt concentration, is comprised between 1 and 10%. Advantageously, the polyol or sugar salt concentration and preferably glycerol salt concentration, is comprised between 1 and 7%. Advantageously, the polyol or sugar salt concentration is from 2% to 5%. The values are expressed by mass based on the total mass of the composition.

According to an alternative, the glycerol salt is a glycerol phosphate, and more specifically a sodium salt, such as for example disodium glycerol phosphate.

The polyol or sugar salt, and preferably the glycerol phosphate, is used for bringing the pH to a basic pH, and then the pH of the composition is adjusted by adding an acid, which has the advantage of providing a thermogelling composition, for which the pH may be modulated very easily and accurately.

When the thermogelling composition does not comprise any gelling agent, the pH may be adjusted by an acid, and for example a weak organic acid or a strong mineral acid (hydrochloric acid). A weak organic acid for example used for adjusting the pH of the composition is acetic acid or glutamic acid.

Thus, the composition according to the invention has a pH greater than or equal to 7, for example greater than or equal to 7.1, and for example a pH from 7.2 to 8.5.

The pH is measured on the final thermogelling composition as a solution, i.e. before the sol-gel transition. The pH is determined by following the method described in the European Pharmacopeia (EP 2.2.3). The pH-meter used is a pH-meter of the Sartorius range provided with a combined glass electrode (PY-P11). The pH measurements are conducted between 20 and 25° C.

Advantageously, the pH is adjustable in the wide range from 6.5 to 8.0.

According to an alternative, the pH is greater than 7.40.

According to a specific alternative, the pH is 7.50+/−0.05.

According to another specific alternative, the pH is 7.20+/−0.05.

According to another specific alternative, the pH is 7.00+/−0.05.

According to a preferred alternative, the composition of the invention has a sol-gel transition at a temperature above 30° C., preferably at a temperature comprised between 30 and 50° C., and preferably between 32 and 45° C., and further preferably between 35 and 40° C.

Advantageously, the thermogelling composition of the invention is in fluid form at room temperature, i.e. between 20 and 25° C.

According to a preferred embodiment, the composition of the invention is fluid at a temperature below 37° C., preferably at a temperature below 35° C., and still preferably at a temperature comprised between 2° C. and 20° C. According to an alternative, the composition of the invention is fluid at the storage temperature, for example from 2 to 8° C., or at an extended room temperature, for example between 15 and 30° C.

According to an alternative, the thermogelling composition of the invention is fluid at a temperature above 0° C. and as a gel at a temperature greater than or equal to 10° C. According to another alternative, the composition of the invention is fluid at a temperature above 0° C. and as a gel at a temperature greater than or equal to 5° C.

According to an embodiment, the composition has an osmolality from 100 to 700 mosm/kg, preferably from 200 to 500 mosm/kg. The osmolality may be expressed in mosm/L, but this is then referred to as osmolarity. When it is an aqueous composition, the density is close to about 1, the osmolality is substantially equal to the osmolarity, like for the compositions of the invention.

According to an alternative, the thermogelling composition according to the invention is iso-osmolar.

According to an alternative, when the composition of the invention is intended to be injected into the plasma of a human being, it is preferable that the osmolality be comprised between 250 and 400, and more specifically between 280 and 350 mosm/kg.

According to another alternative, when the composition of the invention is intended to be injected into the synovial liquid of a human being, it is preferable that the osmolality be comprised between 300 and 490, and preferably between 360 and 470 mosm/kg.

The determination of the osmolality of the solutions is achieved with an automatic micro-osmometer (Osmometer Type 15M of the Loser Messtechnik brand). The piece of equipment is calibrated beforehand with a solution of 300 mosm/kg. The sample is placed in a container provided for this purpose, and is set to the standard measurement temperature.

Advantageously, the thermogelling composition of the invention has in the fluid state a dynamic apparent viscosity comprised between 20 and 800 mPa·s, for example from 40 to 500 mPa·s.

The dynamic apparent viscosity is measured by means of a viscosimeter with a rotating mobile, for example a viscosimeter with a rotary mobile of the Brookfield brand, for example provided with a spindle of the S18 type at a velocity of 5 rpm and at a temperature of 8° C.

According to an alternative, the composition of the invention has an apparent viscosity allowing easy injection in an injection device such as for example a syringe, during its filling. According to an alternative, the composition of the invention has an apparent viscosity allowing easy injection through a fine needle, for example a syringe of 22 gauge, at room temperature. By <<easy>> injection, is preferably meant that the force to be exerted on such a syringe is less than 50 Newtons for causing flow of the thermogelling composition through a needle of 22 gauge, preferably a force of less than 20 Newtons.

The thermogelling composition according to the invention may be diluted, for example in water, optionally buffered. For example it is possible to dilute the composition of the invention in a buffer allowing adjustment of the pH to a physiological pH. More particularly, it is for example possible to dilute the composition of the invention in an acetate buffer (for example a sodium acetate trihydrate buffer of 10 mM) for adjusting the pH to about 7.5.

For a gel, the modulus G' is greater than G". For a solution, the modulus G' is less than G". The sol-gel transition is characterized by the crossover of the G' and G" moduli.

When the solution has a capability of <<thermogelling>>, the modulus G' becomes greater than the modulus G" beyond a certain temperature, and in particular at a temperature less than the physiological temperature (i.e. the temperature at which the product is injected or implanted) or after a certain time after implantation or injection into the body at physiological temperature.

The modulus G' and the modulus G" cross when the temperature increases.

The moduli G' and G" are for example measured with a rotary rheometer with Couette shearing which applies shearing of the fluid between two coaxial cylinders, for example a rheometer ARES of the Rheometrics brand, for example with a frequency of 1 Hz and a deformation of 5%. The measurement of the moduli G' and G" may be conducted at a certain temperature. The measurement of the moduli given here is conducted starting from the product at a certain temperature, for example the storage temperature of the product of 4° C. The product is left to attain a certain temperature naturally, for example the physiological temperature, for example 37° C. without controlling the rate at which the temperature increases.

Advantageously, the storage modulus G' is comprised between 0.001 and 1000, the loss modulus G" is comprised between 0.001 and 1000, G' is greater than G" at the physiological temperature, for example 37° C., after gelling.

According to an alternative, advantageously, the storage modulus G' is comprised between 0.001 and 1000, the loss modulus G" is comprised between 0.001 and 1000, G' is less than G" at the storage temperature and/or at room temperature, and G' is greater than G" at the physiological temperature, for example 37° C., after gelling.

Advantageously, the storage G' and loss G" moduli cross when the product passes from a storage temperature in a refrigerator, for example 2 or 4° C. or from room temperature, for example 18° C. to 25° C., to a physiological temperature, for example 37° C., expressing the sol-gel transition and the thermogelling nature of the system, with a sol-gel transition duration adapted to the targeted application.

Gelling may be achieved by maintaining it at a sufficient temperature and for a sufficient period in order to gel the chitosan solution. This gelling is for example carried out in an oven for example maintained at 40° C. According to an alternative, the thermogelling composition of the invention is in the form of a gel at a temperature of 15° C. According to the present invention, the gelling may occur in situ, i.e. for example after injection into the human or animal body (hot blooded). The gelling notably gives the possibility of positioning the gel in a localized way.

More particularly, the period required for the sol-gel transition is generally comprised between 1 second and 48 hours after passing from the temperature of 2 or 4° C. (storage temperature) to 37° C. (physiological temperature), i.e. for example in situ after injecting the solution into a human or animal body.

According to an alternative, the sol-gel transition is complete after a duration which varies between 5 seconds and 24 hours, preferably less than 4 hours, still preferably less than 2 hours after passing from the temperature of 2 or 4° C. to 37° C.

According to another alternative, gelling occurs instantaneously (gelling occurring as soon as the temperature is increased (and before the measurement)).

According to an alternative, the thermogelling composition is in a gelled form. For example the composition of the invention is stored in a syringe in gelled form.

According to an alternative, the composition should not gel in the injection syringe but gel in si at the desired location. It is possible to carry out several sol-gel transition cycles since the composition according to the invention advantageously has a reversible sol-gel transition. This advantageously allows sterilization of the composition according to the invention by a rise in temperature, i.e. typically with an autoclave. This advantageously gives the possibility of providing a thermogelling composition including the possibility of obtaining gelling is not affected by variations of temperature, notably during storage, transport, or sterilization.

As the composition according to the present invention is notably intended to be injected, the gelling properties are adapted to its injection via a syringe provided with a needle of variable size depending on the targeted application, for example from 19 to 32 gauge, for example 22 gauge. Usually, the person carrying out the injection has to manually press on the piston of the syringe. Therefore, the resistance to compression of the non-gelled fluid has to allow injection as easily as possible. Once it is injected, the composition should gel so as to have the required viscoelastic properties.

According to an alternative, the force required for the flow of the fluid composition in the orifice of a 22 gauge needle is comprised between 1 and 20 Newtons. Preferably, this force is comprised between 2 and 15 Newtons. According to an alternative, this force is comprised between 2 and 8 Newtons.

According to an alternative, the force required for the flow of the fluid composition in the orifice of a 25 gauge needle is comprised between 2 and 15 Newtons. According to an alternative, this force is comprised between 2 and 10 Newtons.

According to an alternative, the force required for the flow of the fluid composition in the orifice of a 27 gauge needle is comprised between 1 and 20 Newtons. Preferably, this force is comprised between 2 and 15 Newtons. According to an alternative, this force is comprised between 2 and 10 Newtons. The injectability is measured by means of a test bench for measuring mechanical properties, for example of the Instron Bluehill brand, provided with a load cell of 500 N. The injection system is specifically designed for measuring the force required for achieving injection of the solution by pushing the piston of the syringe, provided with the needle with the desired diameter. The system has a metal cylinder of a height of 15 cm provided with a vertical slot with a width of 4 cm. The cylinder is surmounted with a square metal plate with a side of 10 cm. This plate is provided with a hole in its middle, with a radius of 0.5 cm. The syringe, provided with a needle of 22 gauge diameter is set to the temperature of 4° C. A constant downward velocity of the piston of the syringe of 1 mm per second is applied.

According to an alternative, the composition comprises a buffer, for example an acetate buffer or a phosphate buffer.

Buffering agents are known to one skilled in the art.

Preferably, the composition comprises a reducing sugar, for example mannitol or sorbitol.

According to an alternative, the present invention relates to a thermogelling composition comprising from 0.1 to 5% by mass of substituted chitosan, and preferably from 1 to 7% of polyol or sugar salt, for example glycerol phosphate, and optionally from 0.1 to 10% of reducing sugar. Advantageously, the composition of the present invention comprises from 0.1 to 1.9% by mass of substituted chitosan and of 2 and 6% by mass of glycerol, preferably glycerol phosphate, and optionally from 0.1 to 2.5% by mass of reducing sugar, based on the total mass of the composition.

According to an alternative, the present invention relates to a thermogelling composition comprising from 0.1 to 5%, and preferably 0.5 to 2.5%, by mass of substituted chitosan, optionally from 0.1 to 10% of reducing sugar, and optionally from 0.1 to 5%, and preferably 0.5 to 2.5% of hyaluronic acid. Advantageously, the composition of the present invention comprises from 0.1 to 2.5% by mass of substituted chitosan, optionally from 0.1 to 2.5% by mass of reducing sugar, and optionally from 0.1 to 5%, and preferably 0.5 to 2.5% of hyaluronic acid, based on the total mass of the composition, said composition preferably not having any glycerol or a glycerol salt.

It is advantageous to use at least one polyol in the composition of the invention (in addition to the polyol salt like glycerol phosphate, if it is present).

Such polyols may for example be selected from the group consisting in: isopropanol, sorbitol, mannitol, alkylene glycol like propylene glycol, poly(alkyl glycol), for example poly(ethylene glycol), fructose, galactose, ribose, glucose, xylose, rhamnulose, sorbose, erythrulose, deoxyribose, ketose, mannose, arabinose, fuculose, fructopyranose, ketoglucose, sedoheptulose, trehalose, tagatose, sucrose, allose, threose, xylulose, hexose, methylthio-ribose, methylthio-deoxy-ribulose, and any of their mixtures.

According to a specific alternative, the reagent which allows the substitution is succinic anhydride. According to this specific alternative, the substituted chitosan is a chitosan succinimide, i.e. a chitosan avec <<succinyl>> groups covalently bound to the nitrogen atom of the amine groups of the D-glucosamine units.

The chitosan is modified by substitution according to a reaction involving a chitosan and a substitution agent in which the chitosan and the substitution agent are reacted therein in order to obtain the substituted chitosan on the D-glucosamine groups.

The invention also relates to a method for preparing substituted chitosan.

This method notably comprises:
a step for dissolving the chitosan in an aqueous solution, preferably water, preferably by adjusting the pH to an acid pH at which the chitosan is soluble;
a step for a substitution reaction of the chitosan with a substitution agent;
a step for stopping the substitution reaction preferably at a degree of substitution of the chitosan ranging from 10 to 50%, expressed in a number of moles of the substituent relative to the number of moles of total units, for example by modifying the pH of the reaction medium, or by precipitation of the chitosan in a <<non-solvent>> in which the substituted chitosan is not soluble;
purification of the substituted chitosan.

By <<non-solvent>> is meant a solvent in which the located chitosan is not soluble, i.e. turbidity is observable to the naked eye. Such solvents are for example polar solvents like for example ethanol, methanol, acetone, etc.

The step for dissolving the chitosan in an aqueous solution may be achieved in water by adding a suitable acid.

During the reaction step, the amount of substitution agent may be adapted according to the desired degree of substitution for the substituted chitosan. During the reaction step, the reaction period may be adapted according to the desired degree of substitution for the substituted chitosan. Advantageously, the reaction is stopped for ending the substitution reaction of the chitosan according to the desired degree of substitution for the substituted chitosan.

Different reactions are known for substituting a chitosan. For example reference may be made to application WO 2010/142507, notably relating to the preparation of chitosan derivatives.

The chitosan substitute may comprise D-glucosamine and N-acetyl-glucosamine units, wherein at least some of the units are grafted (or coupled) with one or several functional groups which may be either identical or different.

According to an alternative, the substituted chitosan comprises glucosamine units and N-acetyl-glucosamine units, said units comprising one or several functional groups. Chemical modifications are for example made by coupling with one or several functions of N-acetyl-glucosamine units, i.e. hydroxyl functions and/or amine functions, and/or glucosamine units, i.e. hydroxy functions and/or amine functions.

According to a particular embodiment, the functional groups present on the substituted chitosan are selected from the group comprising, without being limited thereto, hydrophobic functional groups, hydrophilic functional groups, ionic functional groups and any of their combinations. According to a particular alternative, the hydrophobic functional groups are selected from the group consisting in alkyl, alkenyl, aralkyl, alkaryl groups and any of their combinations. These groups generally comprise between 1 and 100 carbon atoms, and more generally between 1 and 50 carbon atoms, for example between 1 and 25, or further 1 and 10 carbon atoms, one or several of the carbon atoms may be for example replaced with a heteroatom and/or an atom selected from boron, nitrogen, oxygen, sulfur, silicon, germanium, an ester, amide, urea, urethane function or any of their combinations, and wherein one or several hydrogen atoms may be for example replaced with a heteroatom and/or an atom selected from the group consisting in halogen atoms, alkoxy, amide groups and any of their combinations.

According to another embodiment, the hydrophobic functional groups are selected from the group consisting in carboxylic acids, organosulfonic acids, polyethers, amine polyethers, polyesters, sterols, porphyrins and any of their combinations.

According to another alternative, the hydrophilic functional groups are selected from the group consisting in diamines, polyamines, diols, polyols, diacids, polyacids, crown ethers, glymes, polyalkenylethers, polyalkenylamines, polyalkenyletheramines, polyacrylic acids, polyvinylalcohols, and any of their combinations.

According to another particular alternative, the ionic functional groups are selected from the group consisting in metal salts, ammonium salts, phosphonium salts, sulfate salts, carboxylic acid salts, phosphate salts, carboxylic diacids, polycarboxylic acids, a carboxylic acid function being used for forming a covalent bond with the chitosan, diamines, polyamines, an amine function being used for forming a covalent bond with the chitosan, and any of their combinations.

According to a particular alternative, the functional group substituted with chitosan, is an aminoalkyl group. For example, the functional group substituting the chitosan is an aminoethyl group.

According to an alternative, the substituted chitosan is:
an amino-alkyl chitosan such as for example an aminoethyl chitosan, etc. and their equivalents;
a hydrophobisized N-alkyl or O-alkyl chitosan, such as for example an ethanoyl, propanoyl, butanoyl, pentanoyl, hexanoyl, heptanoyl, octanoyl, nonanoyl, decanoyl, or dodecanoyl chitosan and equivalents thereof;
a positively charged chitosan, such as for example a trialkyl ammonium chitosan (par ex. a trimethyl-chitosan or TMC) and equivalents thereof;
an N-(2-hydroxy)propyl-3-trimethylammonium chitosan and its counter-ion such as a chloride and equivalents thereof;
a negatively charged chitosan, such as a chitosan succinimide (succinyl chitosan), an N,O-carboxyalkyl chitosan, an N,O-sulfoalkyl chitosan and equivalents thereof;
a neutral chitosan such as for example N,O-acetyl chitosan, N,O-alkyl chitosan, ethanoyl, propanoyl, butanoyl, pentanoyl, hexanoyl, heptanoyl, octanoyl, nonanoyl, decanoyl, dodecanoyl chitosan and equivalents thereof;
a zwitterionic chitosan, such as for example a chitosan comprising hydrophobic polymers, such as for example an aliphatic polyester, such as homopolymers and copolymers of lactic acid, of glycolic acid, of epsilon-caprolactone, of p-dioxanone of aliphatic and/or aromatic polyesters; of aliphatic polyamides; ethylene polymers and their copolymers; polymers and propylene polymers and copolymers; polycarbonates; polyacrylates and equivalents thereof.

According to a particular embodiment, other derivatives may be used within the scope of the present invention and comprise the O-substituted chitosans, for which the substitution is achieved on the hydroxyl groups of the glucosamine and/or N-acetyl-glucosamine units.

According to an alternative, the chitosan has as a substituent hydrophobic polymers, preferably selected from the group consisting in aliphatic polyesters and aliphatic polyamides, alkene homopolymers or copolymers, such as for example polymers of ethylene or propylene, polycarbonates, polyacrylates, and any of their combinations.

According to an alternative, the chitosan has as a substituent an aliphatic polyester, and in particular a polylactide.

As a substitution method for chitosan, mention may also be made of the reaction described in the American U.S. Pat. No. 7,838,643, and the chitosans resulting therefrom.

Mention may also be made of U.S. Pat. No. 3,953,608.

According to an alternative, it is possible to use as a substitution agent for example an N-alkylating agent, or an alkyl anhydride, optionally comprising one or several unsaturations, optionally comprising one or several heteroatoms and/or functions (such as for example ether, thioether, carboxy, ester, amide, etc) optionally comprising one or several substituents (like an alkyl, amine, hydroxyl, carboxyl, carboxylic acid groups, etc).

According to an alternative, mention may be made as examples of succinic anhydride, glutamic anhydride, acetoxy succinic anhydride, methylsuccinic anhydride, diacetyl tartaric anhydride, diglycolic anhydride, maleic anhydride, itaconic anhydride, citraconic anhydride and any of their mixtures.

Theoretically, any substitution agent giving the possibility of providing a soluble chitosan in the final composition, at a neutral or physiological pH would be suitable.

When the step for stopping the reaction is achieved by precipitation, the purification may consist in separating the insoluble substituted chitosan and of the non-solvent.

After purification, the method of the invention may comprise a step for drying the substituted chitosan, and then optionally milling the latter in order to obtain a powder.

According to a specific alternative, the substitution agent is succinic anhydride. The substituted chitosan is a chitosan succinimide.

The chitosan succinimide may be obtained in the following way:
Dissolving the chitosan in an aqueous solution with a pH of less than 6.5;

The solution is maintained at a temperature comprised between 0° C. and 100° C., preferably between 20° C. and 50° C. and further preferably between 25° C. and 35° C.

After dissolution of the chitosan, adding succinic anhydride, for example as a powder, to the chitosan solution. The amount of succinic anhydride and the number of additions of succinic anhydride are adapted depending on the desired degree of substitution of the substituted chitosan.

After sufficient time so that a minimum degree of substitution is attained, for example after a minimum duration of 15 mins, the reaction is stopped. The reaction may be stopped for example by modifying the pH of the reaction medium or by a precipitation step in a non-solvent such as ethanol, methanol, acetone, . . . .

The substituted chitosan is then advantageously purified, for example by a dialysis technique, or by precipitation/solubilization cycles in a non-solvent, or by a tangential filtration technique.

The purified product is then preferably dried. The product may be dried for example by spray-drying (atomization), or in an oven (in vacuo or at atmospheric pressure), or further by freeze-drying.

The pH of the aqueous solution of chitosan may be adjusted for example with a solution of a weak acid, such as acetic acid, lactic acid, etc., in order to dissolve the chitosan.

The degree of substitution of the chitosan may advantageously vary from 10 to 30%, preferably from 15 to 30%, and still preferably from 15 to 25%, expressed as a number of moles of the substituent relatively to the number of moles of total units. In particular, the present invention relates to a thermogelling composition comprising a substituted chitosan having a degree of substitution from 10 to 30%, preferably from 15 to 30%, and still preferably from 15 to 25%, said composition not comprising any glycerol phosphate.

The degree of substitution of the chitosan succinimide is correlated with the mass ratio of the reagents relatively to the chitosan upon starting the reaction. According to an alternative, the use of a mass ratio of the reagents of more than 0.13 in the case of a chitosan succinimide is preferred. According to an alternative, the use of a mass ratio of the reagents of less than 0.2 in the case of a chitosan succinimide is preferred.

According to a specific alternative, the substitution agent is an agent alkylating amines groups of the D-glucosamine units. The substituted chitosan is advantageously an alkylated chitosan on the D-glucosamine units. As alkylating agents, mention may be made of halogenoalkyls like halogenomethyls, like methyl iodide, methyl bromide, acyl chlorides, such as for example those bearing one or several carboxymethyl, aminoethyl and/or trimethyl groups, etc.

According to this alternative, the substituted chitosan is an N-alkyl chitosan. According to a specific alternative, the substituted chitosan is chitosan bearing a tri-methyl substitution group (N,N,N-trimethyl chitosan, abbreviated as <<TMC>>).

According to an alternative, the alkylated chitosan, preferably TMC, is obtained with a molar ratio of the reagents ranging from 0.1 to 0.35, and preferably from 0.15 to 0.30, expressed as a number of moles of alkylating agent relatively to the number of moles of amine groups initially present in the chitosan.

The chitosan is for example referenced under number CAS 9012-76-4.

The chitosan used for the invention is advantageously of fungal origin, and preferably derived from the mycelium of a fungus of the *Ascomycetes* type, and in particular *Aspergillus niger*, and/or a fungus *Basidiomycetes*, and in particular *Lentinula edodes* (shiitake) and/or *Agaricus bisporus* (button mushroom). Preferably, the chitosan is derived from *Agaricus bisporus*. The chitosan is preferably very pure, i.e. containing little impurities derived from its fungal origin, and of a microbiological quality compatible with its use as an implant or pharmaceutical composition. A method for preparing the chitosan is the one described in patents WO 03/068824 (EP 1 483 299; U.S. Pat. No. 7,556,946).

The prepared chitosan may be of various molecular masses, and generally ranging from 10,000 to 300,000.

According to an alternative, the average molecular mass is comprised between 20,000 and 60,000.

According to another alternative, the average molecular mass is comprised between 60,000 and 100,000.

According to another alternative, the average molecular mass is comprised between 100,000 and 120,000.

According to another alternative, the average molecular mass is comprised between 120,000 and 150,000.

According to another alternative, the average molecular mass is comprised between 150,000 and 220,000.

It is possible to hydrolyze the chitosan in order to reduce its molecular mass.

Preferably here, the average molecular mass is the average molecular mass in viscosity (Mv), calculated from the intrinsic viscosity according to the Mark-Houwink equation. The intrinsic viscosity is measured by capillary viscosimetry with a capillary viscosimeter of the Ubbelohde type, according to the method of the European Pharmacopoeia monography EP2.2.9. The time for the flow of the solution through a suitable capillary tube (Lauda, for example the Ubbelohde 510 01 capillary tube of diameter 0.53 mm) is measured by means of an automatic viscosimeter Lauda Visc, first at the initial chitosan concentration and then for several dilutions, for example according to the recommendations of the EP2.2.9 method. The reduced intrinsic viscosity is inferred therefrom for each of the concentrations. The reduced viscosity is plotted versus temperature, and the value at concentration 0 is extrapolated in order to infer therefrom the intrinsic viscosity. For example the reduced viscosity ($\eta_{réd}$ in ml/g) of i dilutions is plotted versus the concentration C of the i dilutions (g/ml) according to formula 5.

$$[\eta_{réd}] = (t_1 - t_0) - (1 - C).$$  Formula 2.

In order to calculate the average viscosimetric mass, the Mark-Houwink equation is applied with the constants k and alpha as recommended by Rinaudo et al. (Int. J. Biol. Macromol, 1993, 15, 281-285), according to DA of chitosan, according to one of the three following formulae.

$$Mv = ([\eta]/0.082)^{(1/0.76)} \text{ for a DA of 2\%;}$$  Formula 3.

$$Mv = ([\eta]/0.076)^{(1/0.76)}, \text{ for a DA of 10\% (for example 11.5\%);}$$  Formula 4.

$$Mv = ([\eta]/0.074)^{(1/0.76)}, \text{ for a DA of 20\% (for example 21\%).}$$  Formula 5.

For intermediate DA values, a linear interpolation is made for calculating the average viscosimetric mass (Mv).

Preferably, the chitosan used is of an average molecular mass comprised between 120,000 and 150,000 or further comprised between 150,000 and 220,000.

According to a specific alternative, the substituted chitosan preferably has an average molecular mass from 150,000 to 220,000 and a degree of substitution ranging from 10 to 50%, the molecular mass being preferably expressed before substitution.

According to another specific alternative, the substituted chitosan has an average molecular mass from 120,000 to 150,000 and a degree of substitution ranging from 12 to 40%, preferably from 12 to 30%, or even from 20 to 30%, the molecular mass being preferably expressed before substitution.

Advantageously, the chitosan has a degree of acetylation (DA) comprised between 5 and 50%. The degree of acetylation is expressed as a number of N-acetyl-D-glucosamine units relatively to the total number of present N-acetyl-D-glucosamine and D-glucosamine units. According to an alternative, the degree of acetylation is comprised between 20 and 45%.

According to an alternative, the degree of acetylation is comprised between 5 and 20%.

According to an alternative, the degree of acetylation is comprised between 15 and 25%.

According to an alternative, the degree of acetylation is comprised between 20 and 30%.

According to an alternative, the degree of acetylation is comprised between 25 and 40%.

The degree of acetylation is determined by potentiometry. The chitosan is dissolved in a hydrochloric acid solution. The excess of hydrochloric acid which has not reacted with the amine functions of the chitosan is assayed by a titratedsolution of sodium hydroxide. Thus the number of moles of D-glucosamine units present in the chitosan is inferred therefrom and therefore the degree of acetylation by substraction.

The chitosan advantageously has a controlled degree of acetylation. By the terms of <<chitosan having a controlled degree of acetylation>> is meant a product for which the degree of acetylation, i.e. the proportion of N-acetyl-glucosamine units, may be adjusted in a controlled way.

Advantageously, the composition of the invention may also comprise a biopolymer other than the substituted chitosan. According to an advantageous alternative, the biopolymer is a polysaccharide, for example hyaluronic acid or sodium hyaluronate.

Hyaluronic acid may have a molecular mass up to 4 MDa. The molecular mass of hyaluronic acid may be reflected by its intrinsic viscosity. Hyaluronic acid may have an intrinsic viscosity ranging from 1 to 4 $m^3$/kg, and for example be characterized as low (for example about 1 to 2 $m^3$/kg) or high (for example about 2 to 4 $m^3$/kg) molecular mass.

Advantageously, the hyaluronic acid concentration is less than 4%, for example less than 3%, or further for example less than 2% by mass based on the total mass of the composition (m/m).

According to a specific alternative, the concentration of hyaluronic acid is less than 1.9% (m/m), expressed by mass based on the mass of the final composition.

Advantageously, the concentration of hyaluronic acid is comprised between 0.5 and 1.5% (m/m), expressed by mass based on the mass of the final composition. According to a particular alternative, the concentration of hyaluronic acid is of about 0.9%, 1.0%, 1.1%, 1.2%, 1.3%, 1.5% (m/m), expressed by mass based on the mass of the final composition.

The ratio between the chitosan and hyaluronic acid may for example vary from 5 to 95%, for example from 10 to 90%, and further for example from 30 to 70% of substituted chitosan and from 5 to 95%, for example from 10 to 90%, and further for example from 30 to 70% of hyaluronic acid respectively, the percentages expressed based on the: dry mass of substituted chitosan/dry mass of hyaluronic acid). According to an alternative, this ratio between the chitosan and hyaluronic acid is 1/1 (i.e. 50% of chitosan and 50% of hyaluronic acid). According to another alternative, the ratio d between the chitosan and hyaluronic acid is 1.5/0.5 (i.e. 75% of chitosan and 25% of hyaluronic acid).

Advantageously, the thermogelling composition based on substituted chitosan, in the presence of hyaluronic acid forms a gel. Advantageously, according to this alternative, the flow properties of the thermogelling composition may be modulated with the concentration, the ratio between the chitosan and hyaluronic acid, and the molecular mass of hyaluronic acid.

Advantageously, the properties of the gel are retained in the presence of hyaluronic acid.

The gel comprising the substituted chitosan, optionally mixed with hyaluronic acid, advantageously gives the possibility of having good cohesion and good capability of absorbing the shocks of the gel at a low oscillation frequency, for example at a frequency similar to the one imposed on the synovial liquid of a knee during walking (represented by the value of the G' modulus at 0.6 Hz) and a good capability of lubrication of a joint (represented by the viscosity at rest).

The invention also relates to a method for preparing a thermogelling composition according to the invention.

According to an alternative, the method typically comprises:
dissolution of a substituted chitosan in an aqueous solution, preferably water, optionally buffered, preferably with a pH comprised between 6.2 and 8.5 and preferably between 6.5 and 7.5;
optional adjustment of the pH to a physiological pH, for example by adding a buffering agent;
optional adjustment of the osmolality of the composition;
optional adjustment of the viscosity of the composition.

According to an alternative, the method typically comprises:
dissolution of a substituted chitosan in an aqueous solution, preferably water, optionally buffered, preferably at a pH comprised between 6.2 and 8.5 and preferably between 6.5 and 7.5;
optional adjustment of the pH to a physiological pH;
the mixture with a sugar or polyol salt solution, such as for example a solution of glycerol phosphate salt;
optional adjustment of the pH to a physiological pH, for example by adding a buffering agent;
optional adjustment of the osmolality of the composition;
optional adjustment of the viscosity of the composition.

The method may comprise the addition of other components of the composition, if necessary.

According to an alternative, the dissolution of the chitosan is carried out in water comprising a reducing sugar, such as for example mannitol.

According to an alternative, the buffering agent is an acetate buffer.

According to an alternative, the buffering agent is a phosphate buffer.

Advantageously, the method also comprises a subsequent step for filling an injection device, such as for example a syringe, with the composition according to the invention. Advantageously, the injection device, such as for example a syringe may then be subject to sterilization with steam. This device, for example a syringe, may then be packaged, preferably in a sterile way.

It is advantageous to use a chitosan having a sufficient degree of purity for the contemplated application.

The present invention more particularly relates to an injectable composition comprising or consisting in a thermogelling composition according to the invention.

According to an alternative, the composition according to the invention is used as an injectable pharmaceutical composition or as an injectable or implantable medical device.

The present invention more particularly relates to a composition according to the invention for a use for a therapeutic treatment, for example comprising injection of said composition via a sub-cutaneous, intradermal, intraocular, or intra-articular route, for example for repairing or filling at least one body tissue requiring repair or filling.

According to an alternative, the body tissue is selected from tissues belonging to vocal cords, muscles, ligaments, tendons, cartilages, sexual organs, bones, joints, eyes, dermis, epidermis, one or several layers of the skin, mesodermis, or any of their combinations, and more particularly articular joints.

The present invention more particularly relates to a composition according to the invention for treating arthrosis, or repairing a cartilage defect, for example by injecting into the synovial fluid or after mixing with blood and implantation in the cartilage.

The present invention more particularly relates to a medical device, for example a medical implant, characterizing that it comprises or consist in a composition according to the invention.

The present invention may also comprise one or several additives or excipients allowing modulation of its properties. According to a specific alternative, the composition of the invention comprises a suspension of particles, for example solid particles or of a gel.

The present invention also relates to a composition according to the invention for use in an esthetical care or treatment method by dermal filling. This is notably for example the injection of a composition according to the invention via a sub-cutaneous or intra-dermal route.

The present invention also relates to a composition according to the invention for a use in a surface treatment method for the skin by multiple injection via an intra-dermal route. Such compositions may be typically used in dermatology, like treatments for esthetical purposes. Such a method for example has the purpose of re-inflating the skin so as to have it loose its crumpled appearance (treatment of wrinkles and/or lines). Such a treatment may be directed to a subject who wishes to give a rejuvenated aspect to his/her skin.

The present invention also relates to a composition according to the invention for a use in an esthetical care or treatment method in which the composition is a viscosupplement agent. For example the purpose is here to inject at an intra-articular level the composition of the invention notably for limiting friction of the synovial membrane located on either side of the joint.

The present invention also relates to a composition according to the invention for a use as a cell vector, of one or several cell types, and/or one or several active agents. These may be active agents from a pharmaceutical or biological point of view. The composition of the invention may actually be compatible with the presence of cells, preferably living cells. Among the living cells of interest, mention may be made for example of: chondrocytes (articular cartilage), fibrochondrocytes (meniscus), ligament fibroblasts (ligament), skin fibroblasts (skin), tenocytes (tendons), myofibroblasts (muscle), mesenchymatous stem cells, red corpuscles (blood) and keratinocytes (skin). The composition of the invention may also be aimed as a therapeutic vector for targeted delivery and/or controlled release of at least one therapeutic agent.

According to an alternative, blood or plasma or a platelet lyzate or a platelet-rich plasma or any biological fluid are added with the composition of the invention for example allowing an increase in the performances of the product.

According to an alternative, the composition according to the invention is formulated in solid form (for example a film or a porous foam), which solubilizes once it is implanted.

According to an alternative, the composition is formulated as a nebulisable composition (spray).

The present invention also relates to a composition according to the invention for a use in a treatment or esthetical care method of one or several tissues or organs affected by excessive temperature, like in the case of a burn.

The present invention also relates to a composition as an artificial synovial fluid comprising or consisting in the thermogelling composition according to the invention.

The composition according to the present invention gives the possibility of mimicking a healthy synovial fluid or improving a healthy or faulty synovial fluid by trying to improve its shock-absorption properties (identifiable by the elasticity modulus G'), while being easily injectable for filling a syringe for example or being injected into the human or animal body. As an indication, the elastic modulus G' of the healthy synovial liquid is comprised between 40 and 100 Pa, and its loss modulus G" is comprised between 1 and 10 Pa.

According to an alternative, the thermogelling composition is injected in fluid form and then gelled in situ.

According to an alternative, the thermogelling composition is injected as a gel. Advantageously, according to this alternative, the gel is easily injectable through a fine needle.

Generally, the sought ranges of osmolality and pH values in biomedical applications are close to the following values:

Osmolality:
Iso-osmolar to plasma: 285-295 mosm/kg;
Iso-osmolar to the synovial liquid: 404+/−57 mosml/kg, according to <<Clin Orthop Relat Res, 1988, 235, 289-95>> and <<Biochem Biophys Res Comm, 2012, 422, 455-461>>;

pH:
A physiological pH is generally above 6.8, in particular above 7.0, and in particular 7.4 (like for plasma or a synovial liquid).

The pH of plasma is generally 7.4. The pH of synovial liquid is generally 7.768+/−0.044 according to <<J Bone Joint Surg Br, 1959, 41-B(2), 388-400>>; or 7.3 according to <<Acta Orthop Scand, 1969, 40, 634-641>>, or further according to <<Clin Rheumatol 2006, 25, 886-888>>.

The synovial pH in the cases of osteoarthritis is considered as being generally lower than that of healthy synovial fluid.

Quite surprisingly, it was discovered that a thermogelling composition according to the present invention has very good properties when mixed with a synovial fluid, in particular a synovial fluid from the knee of a human being affected with osteo-arthrosis.

Unlike the effect which is observed with the compositions of the prior art based on hyaluronic acid, for which the viscosupplement properties drop when the hyaluronic acid is diluted with the synovial fluid of a patient affected with osteo-arthrosis, thermogelling compositions of the invention, mixed with a synovial fluid retain their gel properties, even after this dilution in the synovial fluid. Still more surprisingly, the thermogelling compositions according to the invention have reinforced rheological properties by mixing with a synovial fluid, in particular a synovial fluid from the knee of a human being affected with osteoarthrosis.

This may be referred to as a synergistic effect between the thermogelling composition of the invention and a synovial fluid.

Thus, the present invention relates to a mixture of a synovial fluid with a thermogelling composition as defined by the present invention, for example according to a thermogelling composition/synovial fluid volume ratio ranging from 20/80 to 80/20 (v/v), and for example 50/50 (v/v).

Advantageously, the composition according to the present invention is sterile. Very advantageously, the composition according to the present invention is sterilized by rising the temperature, preferably in an autoclave.

According to an alternative, the compositions of the invention are transparent or translucent.

By <<translucent>> is meant that an object may be distinguished when its composition is placed between the eye of the observer and the object. By <<transparent>> is meant that it is possible to distinguish alphanumerical characters when the composition is placed between the eye of the observer and the observed characters. Generally, this evaluation is carried out with a thickness of the composition of about 1 cm.

According to an alternative, the composition of the invention is colorless, i.e. in particular a naked eye observer does not ascribe any specific color to the composition.

The invention in particular relates to articles or packaging, preferably sterile, comprising one or several injection devices pre-filled with a thermogelling composition according to the invention. These are typically pre-filled syringes.

The composition of the invention may advantageously be sterilized. According to an alternative, the composition of the invention is sterilized with steam, for example by raising the temperature to a temperature above 100° C., and preferably above 120° C., for example between 121 and 138° C., in an autoclave for a sufficient time for sterilization, for example generally from 15 to 20 minutes.

The invention further covers a composition of the invention in a dry form, notably in a freeze-dried form.

It is notably possible to (re)disperse this freeze-dried composition before use.

The present invention also covers a therapeutic treatment method comprising the injection of a composition according to the invention.

The present invention also covers the use of a composition according to the invention for preparing a pharmaceutical composition, in particular for a therapeutic treatment, for example as more specifically defined by the invention.

The present invention also covers an esthetical care method, in other words non-therapeutic, comprising the injection of a composition according to the invention. For example this is the filling of wrinkles or the filling of one or several damaged visible tissue areas, for example subsequent to an accident or a surgical operation, with an esthetical purpose.

A tissue is an assembly of similar cells and of same origin, grouped in a functional assembly, i.e. contributing to a same function. From among the tissues, mention may be made of: epithelial tissue, connective tissue, muscular tissue and nerve tissue.

By <<composition according to the invention>> or equivalent terms are meant a composition as defined in the present invention, including according to any of the alternatives, particular or specific embodiments, independently or according to any of their combinations, including according to the preferred features.

In the figures:

FIG. 1 illustrates a proton nuclear magnetic resonance spectrum of a chitosan succinimide of the invention.

Other objects, features and advantages of the invention will become clearly apparent to one skilled in the art subsequently to reading the explanatory description which refers to examples which are only given as an illustration and which by no means will limit the scope of the invention.

The examples are an integral part of the present invention and any characteristics appearing to be novel with respect to any prior art state from the description taken as a whole, including the examples, is an integral part of the invention in its function and its generality.

Thus, each example has a general scope.

On the other hand, in the examples, all the percentages are given by mass, unless indicated otherwise, and the temperature is expressed in degrees Celsius unless indicated otherwise, and the pressure is atmospheric pressure, unless indicated otherwise.

EXAMPLES

The precursor chitosans of the substituted chitosans according to the invention have average molecular masses in viscosity (Mv, determined by capillary viscosimetry) and the degrees of acetylation (DA, a proportion of N-acetyl-glucosamine unit, determined by potentiometric titration) comprised in the ranges of Table 1. The molecular mass of a chitosan may also be defined by the dynamic viscosity of a 1% (m/m) chitosan concentration solution in acetic acid with a concentration of 1% (v/v), measured by viscosimetry with a rotating mobile, for example a Brookfield viscosimeter, as indicated earlier.

TABLE 1

Characteristics of the precursor chitosans of the substituted chitosans

| Molecular mass range of the chitosan | Mv range | Viscosity range at 1% (mPa · s) | DA range (mol %) |
|---|---|---|---|
| ultra low | About 20,000-60,000 | 5-20 | 5-20% |
| low | About 60,000-120,000 | 20-50 | 15-25% |
| medium | About 120,000-150,000 | 50-80 | 20-30% |
| high | About 150,000-220,000 | 80-120 | 25-40% |

Example 1—Preparation of a Substituted Chitosan (Chitosane Succinimide, CSS)

In order to obtain the chitosan succinimide of reference CSS5 of Table 2, 10 g of chitosan of known molecular mass and DA are dissolved in 266 ml of an aqueous solution of 1% acetic acid (v/v). The solution is maintained at a temperature of 30° C. 6.75 g of succinic anhydride (SA) are added, which corresponds to a mass ratio of succinic anhydride over chitosan (SA/chitosan) of 0/675, and to a molar ratio of succinic anhydride over the $NH_2$ groups of the chitosan ($SA/NH_2$) of 1/7. After 15 minutes, the pH of the reaction medium may optionally be adjusted to 7.5 by adding 30% soda. The solution is then precipitated from 2.5 liters of ethanol. The precipitate is recovered and again solubilized in water. The substituted chitosan undergoes these precipitation steps from ethanol and then solubilization in water 3 times. At the last precipitation, the precipitate is recovered, pressed and dried in an oven at 60° C. at atmospheric pressure. Once the chitosan succinimide is dry, it is milled in order to obtain a powder. The degree of substitution of the chitosan is determined by proton NMR according to the method described earlier. An NMR spectrum is illustrated by FIG. 1.

The batches of chitosan succinimide used in the examples were prepared in the same way, with the parameters of Table 2.

TABLE 2

Parameters and characteristics of the chitosan succinimide batches

| CSS No. | Mv Range | SA/chitosan mass ratio | SA/NH2 molar ratio | DS (mol %) | pH range for insolubility in water |
|---|---|---|---|---|---|
| CSS1 | medium | 0.119 | 0.3 | 12 | 5.4-6.7 |
| CSS2 | medium | 0.159 | 0.4 | 18 | 6.3-7.3 |
| CSS3 | medium | 0.199 | 0.5 | 25 | 6.1-7.0 |
| CSS4 | medium | 0.262 | 0.6 | 42 | |
| CSS5 | medium | 0.675 | 1.7 | 52 | <5.5 |
| CSS6 | medium | 0.178 | 0.45 | 21 | 5.8-6.9 |
| CSS7 | high | 0.19 | 0.5 | 17 | |
| CSS8 | high | 0.258 | 0.6 | 27 | 4.2-7.0 |
| CSS9 | high | 0.68 | 1.7 | 58 | <5.2 |
| CSS10 | medium | 0.133 | 0.3 | / | 6.4-6.9 |
| CCS11 | medium | 0.133 | 0.3 | / | 5.9-7.1 |
| CSS12 | medium | 0.133 | 0.3 | / | 6.6-7.1 |
| CSS13 | medium | 0.133 | 0.3 | / | 6.5-7.2 |
| CSS14 | medium | 0.133 | 0.23 | / | 6.1-7.6 |
| CSS15 | medium | 0.133 | 0.23 | / | 4.8-6.3 |
| CSS16 | medium | 0.178 | 0.4 | 15 | 5.8-6.9 |
| CSS17 | medium | 0.222 | 0.5 | / | |
| CSS18 | medium | 0.172 | 0.4 | / | 5.5-7 |
| CSS19 | high | 0.2 | 0.5 | / | 5.2-6.3 |

Note:
The addition of sodium beta-glycerol phosphate (65%, Salfic-Alcan, abbreviated as GP) gives the possibility of making the CSS soluble beyond the solubility limit in water. The CSS has a zwitterionic nature. This is not a problem since it is possible to add a small concentration of GP for again finding the soluble nature of CSS.

Example 2—Preparation of a Substituted Chitosan (Trimethyl Chitosan, TMC)

A suspension of 50 g of chitosan in a volume of 800 ml of water is prepared. The suspension is heated to 95° C. A volume of 26.27 ml of 3-chloro-2-hydroxypropyl trimethyl ammonium chloride reagent (abbreviated as CHTAC) is added drop wise to the medium, i.e. a mass and molar ratio of CHTAC/chitosan of 0.31 and 0.5, respectively. After 4 hours of reaction, the reaction medium is diluted with 400 ml of water, and then precipitated from 8.4 liters of ethanol. The precipitate is recovered and again solubilized in water. The substituted chitosan is subject for 3 times to this solubilization/precipitation step from ethanol. At the last precipitation, the precipitate is recovered, pressed and dried in an oven at 60° C. at atmospheric pressure. Once the trimethyl chitosan is dry, it is milled in order to obtain a powder.

The trimethyl chitosan used in the examples were prepared in the same way, with the parameters of Table 3.

TABLE 3

Parameters and characteristics of the trimethyl chitosan batches

| TMC No. | Mv range of the chitosan | CHTAC/chitosan mass ratio | CHTAC/NH$_2$ molar ratio | DS (mol %) |
|---|---|---|---|---|
| TMC1 | medium | 0.37 | 0.5 | 16 |
| TMC2 | medium | 0.79 | 1.05 | 17 |
| TMC3 | medium | 0.37 | 0.5 | 22 |

TABLE 3-continued

Parameters and characteristics of the trimethyl chitosan batches

| TMC No. | Mv range of the chitosan | CHTAC/chitosan mass ratio | CHTAC/NH$_2$ molar ratio | DS (mol %) |
|---|---|---|---|---|
| TMC4 | medium | 0.37 | 0.5 | 26 |
| TMC5 | medium | 0.37 | 0.5 | 28 |
| TMC6 | medium | 0.61 | 0.8 | 36 |
| TMC7 | medium | 1.21 | 1.5 | 75 |

Note:
All these trimethyl chitosans are perfectly soluble in water in the DS range from 16 to 75%.

Example 3—Example of Preparation of a Thermogelling Composition

A chitosan succinimide (CSS2) obtained according to Example 1 is solubilized in water in the following proportions: 0.195 g of chitosan succinimide CSS2 in 14.809 g of water containing 0.5% (m/m) of mannitol. A solution of sodium beta-glycerol phosphate (65%, Salfic-Alcan, abbreviated as GP) at 39.7% (m/m) is prepared. With magnetic or mechanical stirring, 1.49 ml of the GP solution are added to the chitosan succinimide solution. 0.325 ml of acetate buffer 0.5M (pH 3) is added to the chitosan succinimide/GP solution until a given pH is obtained, for example 7.5 in the case of solution No. 2 of Table 4. The osmolality of the final solution finale is measured.

Example 4—Capability of Gelling Chitosan Succinimide Solutions at a Final Concentration of 1.14% (m/m)

The solutions of Table 4 are prepared according to the method described in Example 3.

TABLE 4

«medium» and «high» Mv solutions based on CSS at a concentration of 1.14% (m/m), on GP with a concentration of 4.11% (m/m) and with mannitol at a concentration of 0.5% (m/m); the pH is adjusted to 7.5

| Mv range | Solution No. | CSS No. | SA/chitosan mass ratio | AS/NH2 molar ratio | DS (mol %) | Facilitates injection | Sol-gel transition at 37° C. |
|---|---|---|---|---|---|---|---|
| medium | 1 | CSS1 | 0.12 | 0.3 | 12 | Yes | No |
| | 2 | CSS2 | 0.16 | 0.4 | 18 | Yes | Yes |
| | 3 | CSS3 | 0.20 | 0.5 | | Yes | Yes |
| | 4 | CSS4 | 0.26 | 0.6 | 42 | Yes | No |
| | 5 | CSS5 | 0.68 | 1.7 | 52 | Yes | No |
| high | 6 | CSS6 | 0.18 | 0.4 | | Yes | Yes |
| | 7 | CSS7 | 0.19 | 0.5 | | Yes | Yes |
| | 8 | CSS8 | 0.26 | 0.6 | | Yes | No |
| | 9 | CSS9 | 0.68 | 1.7 | | Yes | No |

The capability of gelling of the thermogelling solution in particular depends on the degree of substitution. The degree of substitution is directly related to the molar ratio between the amine functions present on the chitosan and the amount of succinic anhydride used during the substitution reaction. If the degree of substitution is too high, gelling does not take place (case of solution No. 5). Gelling does not take place if the degree of substitution is too small (case of solution No. 1).

Table 4 shows that for chitosan succinimide, the optimum AS/chitosan mass ratio leading to the thermogelling capability is found to be between 0.12 and 0.26, which is expressed by a DS range from 10 to 45%.

Moreover, the thermogelling solutions of Table 5 are prepared starting from different batches of chitosan succinimide, in order to demonstrate the reproducibility of the preparation of the hydrogels with a mass ratio of 0.13, which gives the possibility of targeting a DS between 14 and 18 mol %. It is seen that the osmolality of the final solution is found between 363 and 447 mosm/kg, and that all the solutions are easy to inject and thermogelling. The presence of mannitol (which is optional for the thermogelling effect) increases the osmolality.

TABLE 5

<< medium >> Mv solutions based on chitosan succinimide at a concentration of 1.14%, on GP at a concentration of 4.11% and on mannitol at a concentration of 0.5%

| Mv range | Solution No. | CSS No. | Osmolality (mosm/kg) | Facilitates injection | Gel at 37° C. |
|---|---|---|---|---|---|
| medium | 10 | CSS10 | 363 | Yes | OK |
| | 11 | CSS11 | 382 | Yes | OK |
| | 12 | CSS12 | 447 | Yes | OK |
| | 13 | CSS13 | 405 | Yes | OK |
| | 14 | CSS14 | | Yes | OK |
| | 15 | CSS15 | | Yes | OK |

Example 5—Capability of the Substituted Chitosan TMC of Gelling at a Final Concentration of 0.9% (m/m)

In the case of trimethyl chitosan with a <<medium>> molecular mass, the optimum degree of substitution for the formulation of the thermogelling gel, for example at a low concentration of 0.9% (m/m), is found to be between 10 and 36% (Table 6).

TABLE 6

Solutions based on TMC at a concentration of 0.9% (m/m) and of GP at a concentration of 3.0% (m/m) (no mannitol); the pH is adjusted to 7.5

| TMC solution No. | TMC No. | DA (mol %) | DS (mol %) | Gel at 37° C. |
|---|---|---|---|---|
| 1 | TMC1 | 16 | 16 | Yes |
| 2 | TMC2 | 16 | 17 | Yes |
| 3 | TMC3 | 15 | 22 | Yes |
| 4 | TMC4 | 18 | 26 | Yes |
| 5 | TMC5 | 18 | 28 | Yes |
| 6 | TMC6 | 17 | 36 | No |
| 7 | TMC7 | 19 | 75 | No |

Example 6—Capability of the Chitosan Succinimide Solutions of Gelling at a Low Concentration, at Osmolality and Physiological pH Values The solubility, the injectability and the thermo-gelling nature of the solutions based on non-substituted chitosan (CS) are compared with those of the solutions based on substituted chitosan (chitosan succinimide CSS), prepared according to the method of Example 2 (Table 7).

TABLE 7

Solutions based on chitosan (CS) or on chitosan succinimide (CSS)

| CS or CSS | Mv range | CS or CSS (% m/m) | GP (%, m/m) | Final pH (adjusted) | Facilitates injection | Gel at 37° C. |
|---|---|---|---|---|---|---|
| CS | high | 1.5% | 6% | 6.8-7.0 | Yes | No |
| CS | high | 1.5% | 6% | 6.7-7.0 | Yes | No |
| CS | high | 2% | 6% | 6.7-7.0 | Yes | Yes |
| CS | high | 2% | 4.1% | 6.7-7.0 | Yes | No |
| CS | medium | 2% | 4.1% | 7.4 | No (precipitates) | No |
| CS | low | 2% | 4.1% | 7.4 | No (precipitates) | No |
| CS | medium | 1.5% | 4.1% | 7.4 | No (precipitates) | No |
| CS | low | 1.5% | 4.1% | 7.4 | No (precipitates) | No |
| CSS | medium | 1.5% | 4.1% | 7.4 | Yes | Yes |

With the non-substituted chitosan of the prior art, the requirement specifications cannot be observed, pH, solubility in water, injectability and gelling at 37° C. simultaneously.

With the chitosan substituted with a succinyl group, it is possible to obtain solubility, injectability and the sol-gel nature even at a lower concentration of GP (with equal polymer concentration), because of the fact that the initial polymer is a substituted chitosan soluble in water, the GP concentration being able to be modulated in order to obtain the desired gelling nature, the osmolality and pH.

Example 7—Capability of the Chitosan Succinimide Solutions of Final Concentration 0.88% of Gelling Over a Wide pH Range In this example, the pH of the solutions was adjusted by adding concentrated acetic acid (96% m/v) in order to minimize dilution of the hydrogel. All the solutions are soluble and easily injectable.

TABLE 8

Solution based on CSS at a concentration of 0.88% (m/m) and on GP at a concentration of 4.16%

| Mv range | CSS No. | pH | Gel at 37° C. |
|---|---|---|---|
| Medium | CSS10 | 6.8 | No |
| | | 7.0 | No |
| | | 7.2 | Yes |
| | | 7.5 | Yes |
| | | 7.6 | Yes |
| | | 8.0 | Yes |

For a given molecular mass and degree of substitution, it is possible to obtain the gelling nature over a wide pH range, for example from 7.2 to 8.0, for example starting with a CSS of a <<medium>> molecular mass and with a mass ratio of 0.133.

Example 8—Capability of Reducing the Concentration of Substituted Chitosan (CSS) while Retaining the Gelling Capability of the Solution

TABLE 9

Solutions based on low concentration CSS

| Mv range | CSS No. | CSS (% m/m) | pH | GP concentration range (% m/m) | Osmolality range | Gel at 37° C. |
|---|---|---|---|---|---|---|
| high | CSS7 | 0.75% | 7.0 | 3.5-4.1 | 310-376 | No |
| | | | 7.5 | 3.4-4.2 | 300-375 | Yes |
| | | 0.88% | 7.0 | 3.4-4.4 | 300-373 | No |
| | | | 7.5 | 3.4-4.4 | 300-380 | Yes |
| medium | CSS17 | 1.34% | 7.0 | 3-3.7 | 300-380 | Yes |
| | | 0.88% | 7.0 | 3.4-3.8 | 300-375 | No |
| | | | 7.5 | 3.4-4.5 | 300-400 | No |
| | | 1.35% | 7.0 | 2.4-2.7 | 300-360 | No |
| | | | 7.5 | 2.4-2.7 | 300-340 | Yes |

It is sometimes advantageous to form final solutions with low concentrations of substituted chitosan in certain applications, for example below 1%, for example 0.85%, while retaining the capability of producing a gel at a physiological temperature, for example 7.5.

Example 9—Injectability of Commercial Products and of Solutions of Substituted Chitosan and GP at Room Temperature This example aims at verifying that the product may easily be injected through a syringe equipped with a small diameter needle, as used for injections via an intra-dermal or intra-articular route. In particular, it is important to be able to easily inject it in small joints like those of the hand.

The force required for injecting the solutions at room temperature during injection of the solution via a 22 gauge needle is evaluated according to the procedure described in the text. The force required for injection after displacement of the piston of the syringe by about 15 mm is measured, which easily allows comparison of the different products with each other. Three solutions of hyaluronic acid intended for intra-articular injection commercially available were tested, and compared with solutions of chitosan succinimide of a <<medium>> molecular mass and of variable concentrations.

TABLE 10

Force required for injection after displacement of the piston by about 15 mm for a 22 gauge needle

| Product | Force (N) |
|---|---|
| Pure water | 0.5 |
| Commercial solution << A >> (hyaluronic acid) | 2 N |
| Commercial solution << C >> (hyaluronic acid) | 6-8 N |
| Solution based on CSS18 at a concentration of 1.0% at pH 7.5 | 3 N |
| Solution based on CSS19 at a concentration of 1.5% at pH 7.5 | 3 N |

It is seen that the chitosan succinimide solutions are as easily injectable through a 22 gauge needle than a commercial solution of hyaluronic acid (A), and more easily injectable than a commercial solution of hyaluronic acid (C).

Example 10—Flow Properties of Commercial Products Based on Hyaluronic Acid and of Thermogelling Solutions Based on Chitosan Succinimide The moduli G' and G" of commercial products based on hyaluronic acid are measured at a temperature ranging from 4° C. to 37° C., overtime, by means of an ARES rheometer, according to the method described earlier. The value of the moduli G' and G" are determined at 60 minutes (Table 11).

TABLE 11

Moduli G' and G" at 60 minutes

| Product | Sol or gel at 4° C. | G' at 37° C. (Pa) | G" at 37° C. (Pa) | Sol or gel at 37° C. (G' versus G") |
|---|---|---|---|---|
| Commercial solution (hyaluronic acid) << A >> | Sol | 0.1 | 1 | Sol (G' < G") |
| Commercial solution (hyaluronic acid) << B >> | Gel | 40 | 38 | Gel (G' > G") |
| Commercial solution (hyaluronic acid) << D >> | Gel | 640 | 120 | Gel (G' > G") |
| Solution based on CSS16 at a concentration of 1.2% at pH 7.5 (solution of Example 12) | Sol | 16 | 1 | Gel (G' > G") |

For the compositions according to the invention, for example for the composition based on chitosan succinimide and GP at pH=7.5, the modulus G' crosses the modulus G" after a few seconds, and G' is greater than G" beyond the time at which the crossover occurs, characterizing a fast sol-gel transition when the product passes from 4° C. to 37° C.

The tested commercial compositions based on hyaluronic acid are not thermogelling.

Example 11—Effect of Intra-Articular Injection of a Solution of Chitosan Succinimide in Rabbits after Transection of the Anterior Ligament The solution of this example is a sterilized solution comprising 1.2% (m/m) of chitosan succinimide of degree of substitution of 15% and with a <<medium>> molecular mass (No. CSS16 of Table 2), 3.5% (m/m) of GP, 0.4% (m/m) of D-mannitol and 11 mmol/l of sodium acetate trihydrate. The solution is sterilized with steam with an autoclave, the concentration is adjusted by dilution by a factor of 1.33, and then the solution is conditioned in a syringe. After sterilization and dilution, the pH is equal to 7.5, the osmolality is equal to 380 mosm/kg, and the apparent dynamic viscosity is equal to 126 mPa·s at 9° C.

A transection of the anterior ligament, called an <<anterior cruciate ligament transection (ACLT)>>, in rabbits causes consistently and in a well documented way, symptomatic modifications of osteoarthrosis (OA), i.e. cracks of the cartilage, significant lesions and inflammation of the synovial membrane without any loss of cartilage over the whole height of the joint. This model is in particular used for studying the effects of novel therapies like intra-articularly injected viscosupplements on the structure of the cartilage, the initial lesions may be of highly variable origin and nature (in Laverty et al. Osteoarthr Cartil, 2010; Edouard et al. Phys Ther Sport, 2013; Mainil-Varlet et al. Cartilage, 2013; Oprenyeszk et al. Osteoarthr Cartil, 2013).

In this model, erosion of the cartilage appears as soon as 4 weeks after the surgical intervention which consists of carrying out a transection of the anterior ligament of the right knee. It is recommended to conduct the study up to 8 weeks after the intervention, which gives the possibility of obtaining erosion of the cartilage in at least 40% of the femoral condyles. The intra-articular injection of the product to be tested is made after appearance of the first signs of osteoarthrosis, i.e. 1 week after surgery on the knee having been subject to the transection. The right knee of 10 animals of the test group received an injection of 600 µl of the thermogelling solution to be tested. The right knee of 9 animals of the <<control>> group received an injection of 600 µl of 0.9% saline solution. The products are injected into the joint of the knee of the rabbits via a syringe provided with a 22 gauge needle.

The capability of the product of slowing down or stopping the progression of arthrosis induced by surgery is characterized by examining several macroscopic, histological and radiological indicators, characterized according to the scores recommended by OARSI (in Laverty et al. Osteoarthr Cartil 2010). The results of the radiology of the joints are evaluated according to the Kellgren & Lawrence scale, on the basis of the presence of osteophytes and of the inter-articular space.

The study is a double blind study, i.e. neither the surgeon which proceeds with the operation and with the injection of the products to be tested, nor the persons which carry out macroscopic observations during the life of the animals and at the moment of their euthanasia, nor the persons which analyze the macroscopic or histological results and establish the statistical calculations are aware of the correspondence between the numbers of the animals and the groups per tested product. This correspondence is only given once the calculations are completed and drawn up by an independent person. The results are reported in Tables 11 to 13.

As compared with the injection of a saline solution, the injection of the thermogelling solution HG gives the possibility of decreasing in a statistically significant way all the indicators of osteoarthrosis at 8 weeks, as demonstrated by a decrease of the inter-articular space and of the presence of osteophytes visible in a radiological examination (Table 12, according to the Kellgren & Lawrence scale), the decrease in the severity and size of the lesions of the cartilage which appear on the lateral side of the joints (Table 13), and the decrease in the inflammatory infiltrates of the synovial membrane (Table 14). No undesirable secondary effect of the thermogelling solution is detected relatively to the control group, expressing good tolerance to the product under the conditions of the study.

TABLE 12

Radiological score according to the Kellgren & Lawrence scale (from 0 to 4) evaluating the inter-articular space and the presence of osteophytes (p-value calculated by the non-parametric method of the U test of Mann-Whitney)

| Radiological score according to K&L (0-4) | Saline solution | Thermogelling solution |
|---|---|---|
| Number of animals | 9 | 10 |
| Number of observations | 9 | 10 |
| Average score | 2.0 | 0.0 |
| Median score | 1.8 | 0.4 |
| Min score | 0.0 | 0.0 |
| Max score | 3.0 | 3.0 |
| Standard deviation | 0.7 | 0.6 |

TABLE 12-continued

Radiological score according to the Kellgren & Lawrence scale (from 0 to 4) evaluating the inter-articular space and the presence of osteophytes (p-value calculated by the non-parametric method of the U test of Mann-Whitney)

| Radiological score according to K&L (0-4) | Saline solution | Thermogelling solution |
|---|---|---|
| Difference between both groups and p-value (probability) | — | Statistically significant p-value = 0.0079 |

TABLE 13

Overall macroscopic score evaluating the size and the severity of the lesions of the side compartments of the cartilage of the tibial plates and femoral condyles (p-value calculated by the non-parametric method of the Mann-Whitney U test)

| Overall macroscopic score (size and severity of the lesions) | Saline solution | Thermogelling solution |
|---|---|---|
| Number of animals | 9 | 10 |
| Number of observations | 18 | 20 |
| Average score | 32.0 | 17.5 |
| Median score | 32.8 | 21.4 |
| Min score | 3.0 | 3.0 |
| Max score | 68.0 | 44.0 |
| Standard deviation | 13.4 | 10.2 |
| Difference between the 2 groups and p-value (probability) | — | Statistically significant p-value < 0.0041 |

TABLE 14

Score of the inflammatory infiltrate of the synovial membrane evaluated by histology (p-value calculated by the non-parametric method of the Mann-Whitney U test)

| Score of the inflammatory infiltrate (0-5) | Saline solution | Thermogelling solution |
|---|---|---|
| Number of animals | 9 | 10 |
| Number of observation | 27 | 28 |
| Average score | 2.0 | 1.4 |
| Median score | 2.6 | 1.8 |
| Min score | 1 | 0.5 |
| Max score | 5 | 5.0 |
| Standard deviation | 1.0 | 1.0 |
| Difference between the 2 groups and p-value (probability) | | Statistically significant p-value = 0.0011 |

Examples 12-24

In Examples 12 to 24, the following methods and procedures were used:

Flow Properties

The flow properties are measured by means of a rheometer <<Discovery Hybrid DHR-2>> (TA Instrument; see for example: http://www.tainstruments.com), equipped with a Peltier Plate and a solvent trap. The geometry used is the steel Peltier Plate with the diameter of 25 mm, and the distance between the plate and the Peltier is set to 0.7 mm. The measurements are conducted at 37° C., except for the temperature sweeping experiment described in Example 12. The measurements are conducted according to the following procedures:

Identification of the Viscoelastic Linear Region by Deformation Sweeping

A deformation sweeping test is first carried out for identifying the viscoelastic linear region (LVER) of each product, at 37° C.

Frequency Sweeping in a Low Oscillatory Mode

Frequency sweeping between 0.01 rad/s and 100 rad/s is carried out in the <<LVER>> region of each product, at a deformation of 0.9%, with the low amplitude oscillatory mode (<<small amplitude oscillatory shear>>, SAOS) at 37° C. The following characteristics are measured versus the sweeping frequency: elastic modulus (G'), loss modulus (G"), crossover frequency of the moduli G' and G" (<<crossover frequency>>) and complex viscosity ($\eta^*$). In particular, the value of the elastic module G' is determined at the frequency of 0.6 Hz, which correspond to the frequency applied to the synovial liquid of the knee during walking.

Flow Sweeping

The viscosity at rest is determined by the flow sweeping mode. The product is balanced for 1 minute at 37° C. A shear rate from 0.001 s' to 10 s' is applied for measuring the viscosity versus the shear rate. From the curve obtained over this shear rate range, the viscosity at rest is determined by extrapolating the value of the viscosity at zero shear. In the case when the correlation coefficient is less than 0.98, the viscosity at the lower shear rate (0.001 $s^{-1}$) is reported.

Degree of Substitution (NMR Measurement)

The degree of substitution is determined in the examples which follow by proton nuclear magnetic resonance (NMR) in solution in an aqueous medium, by means of a magnetic resonance spectrometer, for example a Bruker spectrometer of frequency 400 MHz. The samples are prepared in the following way: 5 to 6 mg of substituted chitosan are dissolved in 1 ml of deuterated water. 2 µl of deuterated hydrochloric acid or sodium borate are added to the substituted chitosan solution in order to attain a pH range suitable for the analysis. The suitable pH range depends on the nature of the substituent and may be of 8.5 for example with sodium borate and between 3 and 4 with HCl 12M. The spectrum is recorded at a temperature of 70° C., with a number of scans ranging from 64 to 256 and a relaxation time ranging from 1 to 8 seconds. The obtained spectrum is treated by deconvolution in order to determine the value of the integral of the areas of the signals of interest so as to be able to calculate the degree of substitution of the substituted chitosan.

The substituted chitosans which were used in Examples 12 to 24 were prepared and characterized according to the methods described earlier (Table 15). The molecular mass of the chitosan is defined by the viscosity of a solution of chitosan at a concentration of 1% (m/m) in acetic acid with a concentration of 1% (v/v).

TABLE 15

Characteristics of the substituted chitosans and of the precursor chitosans of these substituted chitosans.

| Substituted chitosans | | Precursor chitosans | | |
| --- | --- | --- | --- | --- |
| Reference | DS (mol %) | Reference | Mw range | Viscosity at 1% (mPa · s) |
| Chitosan succinimide | | | | |
| CSS20 | 29** | CS1 | Medium | 40 |
| CSS21 | 18* | CS2 | | 60 |
| CSS22 | 19** | CS3 | | 63 |
| CSS23 | 19** | | | |
| CSS24 | 20** | CS4 | | 72 |
| CSS25 | 20* | CS5 | | 78 |
| CSS26 | 20* | | | |
| CSS27 | 25* | | | |
| CSS28 | 30* | | | |
| CSS29 | 20** | | | |
| CSS30 | 28** | CS4 | | 72 |
| Trimethyl-chitosan | | | | |
| TMC8 | 26** | CS2 | Medium | 60 |

*Degree of substitution estimated on the basis of the targeted value during the substitution reaction;
**degree of substitution measured by proton NMR according to the method described earlier.

In the examples which follow, the substituted chitosan formulations are prepared according to the following protocol:

Solubilize the powder of substituted chitosan to the intended concentration containing the desired concentration of sorbitol or mannitol;

Add a mother solution of phosphate buffer (100 mM) in order to obtain osmolality comprised between 280 and 400 mosm/kg;

Add glacial acetic acid, until a pH between 7.2 and 8.5 is obtained.

All the following examples relate to formulations sterilized with an autoclave, except if <<before autoclave>> is mentioned, according to the following procedure:

Put the solution in a suitable container and sterilize with the autoclave at 121° C. for 20 minutes.

Table 16 contains the lists of formulations based on substituted chitosan described in Examples 12 to 22.

TABLE 16

| Formulations based on substituted chitosan | | | | | | | |
| --- | --- | --- | --- | --- | --- | --- | --- |
| | Substituted chitosan | | Hyaluronic acid | | | Sugar | |
| Formulation (reference) | Ref | Concentration (%, m/m) | Ref | Concentration (%, m/m) | GP | Mannitol or sorbitol | Concentration (%, m/m) |
| Chitosan succinimide | | | | | | | |
| 17-008 | CSS29 | 2% | / | / | / | Sorbitol | 0.5% |
| 16-27A | | 1.75% | / | / | / | Sorbitol | 0.5% |

TABLE 16-continued

Formulations based on substituted chitosan

| | Substituted chitosan | | Hyaluronic acid | | | Sugar | |
|---|---|---|---|---|---|---|---|
| Formulation (reference) | Ref | Concentration (%, m/m) | Ref | Concentration (%, m/m) | GP | Mannitol or sorbitol | Concentration (%, m/m) |
| 16-27B | | 1.5% | / | / | / | Sorbitol | 0.5% |
| 8-147D | CSS2 | 2% | / | / | / | Mannitol | 0.5% |
| 17-032-1 | CSS26 | 2% | / | / | / | Sorbitol | 0.5% |
| 17-032-2 | | 1.25% | / | / | / | Sorbitol | 0.5% |
| 17-033C-1 | CSS27 | 2% | / | / | / | Sorbitol | 0.5% |
| 17-033C-2 | | 1.25% | / | / | / | Sorbitol | 0.5% |
| 17-033B-1 | CSS28 | 2% | / | / | / | Sorbitol | 0.5% |
| 17-033B-2 | | 1.25% | / | / | / | Sorbitol | 0.5% |
| 8-145A | CSS25 | 2% | / | / | / | Mannitol | 0.5% |
| 8-147B | | 2% | / | / | / | Mannitol | 0.5% |
| 8-147C | | 2% | / | / | / | Mannitol | 0.5% |
| 16-008A | CSS23 | 2% | / | / | / | Sorbitol | 0.5% |
| 16-008B | | 2% | / | / | Yes | Sorbitol | 0.5% |
| 14-084 | CSS29 | 1% | H34 | 1% | / | / | / |
| 14-49A1 | CSS25 | 0.33% | H34 | 1.67% | / | / | / |
| 14-49A3 | | 0.5% | | 1.5% | / | / | / |
| 14-49A2 | | 0.67% | | 1.33% | / | / | / |
| 14-49A4 | | 1.0% | | 1.0% | / | / | / |
| 14-49A5 | | 0.5% | H22 | 1.5% | / | / | / |
| 14-49A6 | | 1.0% | | 1.0% | / | / | / |
| 013-009 | CSS21 | 1% | / | / | Yes | / | / |
| 13-006E4 | | 1.3% | / | / | Yes | / | / |
| 13-010 | | 1.5% | / | / | Yes | / | / |

Example 12—Thermogelling Nature of Formulations Based on Chitosan Succinimide Sweeping in temperature is carried out in order to follow the time-dependent change in the elastic (G') and loss (G") moduli of different formulations based on chitosan succinimide depending on the temperature (Table 17), by means of the rheometer <<Discovery Hybrid DHR-2>> (TA Instrument) equipped with a Peltier element and a geometry of the parallel steel plate type of 25 mm, with a distance of 0.7 mm. The rise in temperature is preceded with pre-shearing in order to standardize the differences between samples during the setting into place of the sample on the rheometer. The deformation, the temperature rise rate and the frequency are adjusted according to each tested sample (Table 17).

crosses G" varies depending on the composition of the formulation and on the molecular characteristics of the chitosan succinimide.

Example 13—Formulations of Low Substituted Chitosan Concentration, with View to Injection Through Very Fine Needles (29 G and 30 G)

The elastic (G') and loss (G") moduli of formulations based on substituted chitosans (succinimide and trimethyl) are measured with an ARES rheometer with a <<cone-plate>> Peltier geometry at a distance of 50 µm and an angle of 0.04 radians, at a frequency of 10 Hz at 37° C., with 3% deformation, according to the method described earlier

TABLE 17

Elastic modulus (G') and loss modulus (G") of formulations based on chitosan succinimide at different temperatures.

| Reference (formulation) | Pre-shearing (frequency, duration) | Deformation (%) | Frequency (rad/s) | Rise in temp (° C./min) | G' and G" modulus (Pa) | | | | | | |
|---|---|---|---|---|---|---|---|---|---|---|---|
| | | | | | 2.6° C. | 3.2° C. | 5° C. | 10° C. | 20° C. | 25° C. | 37° C. |
| 17-008 | 10 rad/s 30 s | 250% | 2.5 | 5 | G' = 22.94 G" = 24.35 | G' = 24.9 G" = 24.0 | G' = 29 G" = 23 | G' = 34 G" = 32 | G' = 43 G" = 23 | G' = 47 G" = 25 | G' = 54 G" = 36 |
| 16-27A | 25 rad/s 90 s | 160% | 3 | 5 | G' = 7.7 G" = 8.2 | G' = 8.1 G" = 8.0 | G' = 9 G" = 7 | G' = 10 G" = 7 | G' = 14 G" = 6 | G' = 16 G" = 6 | G' = 23 G" = 7 |
| 16-27B | 25 rad/s 90 s | 160% | 3 | 5 | / | / | G' = 6 G" = 7 | G' = 8 G" = 7 | G' = 11 G" = 6 | G' = 13 G" = 5 | 5G' = 21 G" = 5 |
| 14-084 | 20 rad/s 120 s | 25% | 0.1 | 1.5 | / | / | G' = 46 G" = 51 | G' = 51 G" = 50 | G' = 52 G" = 48 | G' = 52 G" = 47 | G' = 62 G" = 42 |

It is understood from this example that for all the tested formulations based on chitosan succinimide, the elastic modulus G' becomes greater than the elastic modulus G" from a certain temperature, which shows the thermo-gelling nature of the formulations. The temperature at which G'

(Table 18a). The dynamic viscosity is measured with a viscosimeter with a rotary mobile (Brookfield), as illustrated earlier (Table 18a). The force required for injecting the formulations through the 29 and 30 gauge needles is measured as described earlier (Table 18b).

TABLE 18a

Flow properties and viscosity

| Formulation (Reference) | Type | Gel (G' > G") | G' at 900 s (Pa) | Dynamic viscosity (mPa · s) |
|---|---|---|---|---|
| 13-009 | CSS 1% | Gel after 40 s | 100 | 439 |
| 13-006E4 | CSS 1.3% | Gel | 153 | 744 |
| 13-010 | CSS 1.5% | Gel | 95 | 1621 |
| 13-008 | TMC 1.1% | Gel | 70 | 241 |
| 13-006F4 | TMC 1.3% | Gel | 137 | 418 |

TABLE 18b

Injectability (force required for the injection) in Newtons

| | Size of the needle | |
|---|---|---|
| Ref | 29 G Thin-walled | 30 G Normal-walled |
| 13-009 | 3.6 N | 7.5 N |
| 13-006E4 | 6 N | 11 N |
| 13-010 | 5.75 N | 12.5 N |
| 13-008 | 2.7 N | 5.5 N |
| 13-006F4 | 4.1 N | 8.9 N |

It emerges that easily injectable formulations through very fine needles are obtained, for example suitable for sub-cutaneous, intra-dermal injections, or further for micro-injections practiced at the epidermis notably for rejuvenation of the skin, or further intra-camerular injections for ophthalmology, while retaining the gel properties with good elasticity and viscosity.

Example 14—Flow Properties of Commercial Viscosupplements

The flow properties of commercial products based on hyaluronic acid of the non-cross-linked (VS1 and VS2) or cross-linked with covalent bonds (VS3) intended for viscosupplementation, are measured by means of the rheometer <<Discovery Hybrid DHR-2>> (TA Instrument) at 37° C. in an oscillatory mode, according to the method described earlier. The crossover frequency is determined between the moduli G' and G", the value of G' at the frequency of 0.6 Hz which corresponds to the walking frequency. The viscosity at rest is determined in the flow sweeping mode, according to the method described earlier.

TABLE 19

Flow properties of commercial viscosupplements

| Reference | Type of cross-linking | HA concentration | Crossover frequency (Hz) | G' at 0.6 Hz (Pa) | Viscosity at rest (Pa · s) |
|---|---|---|---|---|---|
| VS1 | No cross-linking | 2% | 5.2 Hz | 114 | 212 |
| VS2 | No cross-linking | 1% | No crossover | 0.05 | 7 |
| VS3 | Covalent cross-linking | 0.8% | No crossover | 114 | 835 |

From this example it is understood that the flow behavior of the viscosupplements based on hyaluronic acid depend on their composition and on molecular characteristics of the hyaluronic acid, notably on the structure either cross-linked by covalent bonds or not.

Example 15—Formulations of Chitosan Succinimide at Different Glycerophosphate Concentrations The flow properties of formulations based on chitosan succinimide of a <<medium>> molecular mass (reference CSS25) are measured at the concentration of 2% (m/m) and of glycerophosphate (GP) of variable concentration, by means of the rheometer <<Discovery Hybrid DHR-2>> (TA Instrument) at 37° C. according to the methods described earlier (Table 20).

TABLE 20

Flow properties of formulations based on chitosan succinimide at 2% (m/m) versus the GP concentration

| Formulation (reference) | GP % (m/m) | G' > G" at 0.6 Hz | Crossover frequency | G' at 0.6 Hz (Pa) | Viscosity at rest (mPa · s) |
|---|---|---|---|---|---|
| 8-145A | 4% | Yes | No | 526 | 8160 |
| 8-147B | 2% | | crossover | 298 | 29000 |
| 8-147C | 1% | | | 164 | 14460 |
| 8-147D | 0% | | | 184 | 12034 |

It emerges from this example that:
- A solution of chitosan succinimide with a degree of substitution of 20% and a molecular masse of the <<medium>> type may form a gel without adding GP;
- The cohesion of the gel may be increased by adding GP in an increasing concentration;
- The lubrication capability (viscosity at rest) attains a maximum when the GP proportion is increased.

Example 16—Formulations Based on Chitosan Succinimide of Variable Degree of Substitution and Concentration Solutions of chitosan succinimide with variable concentrations are prepared as described earlier, starting with chitosan succinimide with different degrees of substitution (DS) (references CSS26, CSS27, CSS28) and of same molecular mass (<<medium>>), without GP. The flow properties of the formulations are measured by means of the rheometer <<Discovery Hybrid DHR-2>> (TA Instrument) at 37° C. according to the methods described earlier (Table 21).

TABLE 21

Flow properties of formulations based on chitosan succinimide versus the DS

| Formulation (reference) | Concentration (%, m/m) | CSS (reference) | DS* (mol %) | G' > G" at 0.6 Hz | G' at 0.6 Hz (Pa) | Viscosity at rest (mPa · s) | Crossover frequency |
|---|---|---|---|---|---|---|---|
| 17-032-1 | 2% | CSS26 | 20% | Yes | 299 | 10500 | No crossover |
| 17-032-2 | 1.25% | | | | 58 | 3400 | |
| 17-033C-1 | 2% | CSS27 | 25% | | 52 | 2500 | |
| 17-033C-2 | 1.25% | | | | 9 | 200 | |
| 17-033B-1 | 2% | CSS28 | 30% | | 30 | 1000 | |
| 17-033B-2 | 1.25% | | | | 10 | 130 | |

*DS estimated as described earlier

It emerges that:

Gels are obtained for all the formulations prepared starting with CSS with a DS of 20, 25 and 30%;

The cohesion and the viscosity at rest is modulated by varying the DS and the CSS concentration, for a same molecular mass (medium).

Example 17—Formulations Based on Chitosan Succinimide and Hyaluronic Acid

A solution of chitosan succinimide (reference CSS25) at 2% (m/m) is prepared as described earlier. A solution of hyaluronic acid (HA) at 2% (m/m) is prepared by solubilizing HA and mannitol in a phosphate buffer, in order to obtain an osmolarity between 280 and 400 mosm/kg and a pH between 7.2 and 8.5. A HA of high molecular mass is used (reference H34, intrinsic viscosity of 3 m$^3$/kg, as provided by the supplier) or of low molecular mass (reference H22, intrinsic viscosity of 1.55 m$^3$/kg). The solutions are then mixed in different proportions by mass. They are sterilized with an autoclave as described earlier. The flow properties of the formulations are measured by means of the rheometer <<Discovery Hybrid DHR-2>> (TA Instrument) at 37° C. according to the methods described earlier (Table 22).

TABLE 22

Flow properties of formulations based on chitosan succinimide and hyaluronic acid

| Formulation (reference) | HA (reference) | CSS conc. (%, m/m) | HA conc. (%, m/m) | Crossover frequency | G' at 0.6 Hz (Pa) | Dynamic viscosity at 0.6 Hz (mPa · s) |
|---|---|---|---|---|---|---|
| 8-147D | / | 2.0% | / | No crossover | 650 | 164 |
| 49-A1 | H34 | 0.33% | 1.67% | 1.2 Hz | 48 | 19 |
| 49-A3 | | 0.5% | 1.5% | 1.2 Hz | 36 | 14 |
| 49-A2 | | 0.67% | 1.33% | 1.1 Hz | 35 | 14 |
| 49-A4 | | 1.0% | 1.0% | No crossover | 47 | 15 |
| 49-A5 | H22 | 0.5% | 1.5% | 13 | 7 | 5 |
| 49-A6 | | 1.0% | 1.0% | 0.1 | 13 | 5 |

From the results it is understood that the flow properties of the gels formed by the mixture of CSS and HA may be modulated with the concentration, the proportion between CSS and HA and the intrinsic viscosity of the HA. The high viscosity HA gives the possibility of obtaining the gel which has the highest G' and dynamic viscosity at the operating frequency (0.6 Hz). Further, under certain conditions, there is no crossover of the moduli G' and G", showing that the gel is formed regardless of the shearing frequency.

Example 18—Synergy with the Synovial Liquid of the Knee of Arthrosic Patients With their consent, synovial liquid (SF) of four voluntary adult patients affected with osteo-arthrosis of the knee is sampled before implantation of a prosthesis (SF1 to SF4). It is mixed with different solutions based on chitosan succinimide or with different commercial viscosupplements in a mass ratio of 1/1, and then the flow properties of the mixtures are measured by means of the rheometer <<Discovery Hybrid DHR-2>> (TA Instrument) at 37° C. according to the methods described earlier (Table 23).

TABLE 23

Flow properties of the synovial liquid of the knee of four patients affected with osteo-arthrosis, and of formulations of chitosan succinimide or of commercial viscosupplements, before and after mixing with the synovial liquid at a volume ratio of 50/50 (v/v).

| | Formulation alone | | | Formulation mixed with the synovial liquid | | | |
|---|---|---|---|---|---|---|---|
| Formulation (reference) | G' at the frequency of 0.6 Hz (Pa) | Viscosity at rest (Pa · s) | SF (reference) | G' > G" at the frequency of 0.6 Hz | G' at the frequency of 0.6 Hz (Pa) | Viscosity at rest (Pa · s) | Crossover frequency (Hz) |
| / | / | / | SF1 | Yes | 3 | ND | 0.04 Hz |
| / | / | / | SF2 | Yes | 1 | ND | 0.3 Hz |
| / | / | / | SF3 | Yes | 0.8 | 7 | 0.4 Hz |
| / | / | / | SF4 | Yes | 1 | 1 | 0.6 Hz |
| VS1 | 115 | 210 | SF2 | No | 10 | 20 | 1.9 Hz |
| VS2 | 0 | 7 | SF2 | No | 0 | 20 | 0.8 Hz |
| VS3 | 115 | 830 | SF2 | Yes | 9 | 90 | No |
| 8-147D | 130 | 2580 | SF2 | Yes | 89 | 11100 | crossover |
| 14-63B7 | 150 | 5400 | SF4 | Yes | 41 | 1400 | |
| 8-145D | 30 | 4200 | SF1 | Yes | 12 | 1500 | No |
| 8-145C | 60 | 5600 | SF1 | Yes | 55 | 6650 | crossover |
| 8-145A | 520 | 8200 | SF1 | Yes | 450 | 64500 | |

It emerges from this example that:
- the synovial liquid of patients affected with osteoarthrosis at the knee is a gel with low flow properties; the viscosupplements and the formulations based on chitosan succinimide have superior properties;
- the viscosupplements based on HA have their flow properties drop when diluting them with SF;
- the formulations based on CSS retain their gel properties after dilution in the synovial liquid;
- the formulations based on CSS have reinforced flow properties by mixing with the synovial liquid of a voluntary adult affected with osteoarthrosis, unlike the commercial viscosupplements based on HA either cross-linked or not. There occurs probably an interaction with the components of the synovial liquid, for example hyaluronic acid or aggrecans.

Example 19—Reproducibility of the Formulations Based on Chitosan Succinimide Starting with Several Batches of Chitosan Succinimide Chitosan succinimide solutions with variable concentration are prepared as described earlier, starting with different batches of CSS with similar degrees of substitution from 19 to 28% (references CSS22, CSS24, CSS25, CSS29 and CSS30) and of similar molecular masses (medium), without GP. Their flow properties are measured by means of the rheometer <<Discovery Hybrid DHR-2>> (TA Instrument) at 37° C. according to the methods described earlier, before and after treatment with an autoclave (Table 24a and 24b).

TABLE 24a

Before an autoclave

| Ref CSS | DS (mol %) | Formulation (reference) | Crossover frequency (Hz) | G' at the frequency of 0.6 Hz (Pa) | Viscosity at rest (Pa · s) |
|---|---|---|---|---|---|
| CSS25 | 20 | 2 (008-147E) | No | 170 | 12300 |
| CSS29 | 20 | 5 (016-013A) | crossover | 159 | 8000 |
| CSS30 | 28 | 1 | ND | ND | ND |
| CSS24 | 20 | 3 (016-006B) | No | 75 | 3600 |

TABLE 24a-continued

Before an autoclave

| Ref CSS | DS (mol %) | Formulation (reference) | Crossover frequency (Hz) | G' at the frequency of 0.6 Hz (Pa) | Viscosity at rest (Pa · s) |
|---|---|---|---|---|---|
| CSS22 | 19 | 4a (016-006C1) | crossover | 95 | 4000 |
| | | 4b (016-008A) | | 106 | 4800 |

TABLE 24b

After an autoclave

| Formulation (reference) | Crossover frequency | G' at the frequency of 0.6 Hz (Pa) | Viscosity at rest (Pa · s) | Injectability (27 G needle, N) |
|---|---|---|---|---|
| 2 | ND | ND | ND | ND |
| 5 (016-014A) | No crossover | 129 | 6745 | ND |
| 1 | ND | ND | ND | 9 N |
| 3 (016-010B) | No | 133 | 8400 | 9 N |
| 4a (016-010C) | crossover | 167 | 7800 | 10 N |
| 4b (016-010D) | | 109 | 5500 | 13 N |

It is observed from this example that:
- The treatment with the autoclave retains the gel nature, the elastic modulus and the viscosity at rest of the formulations;
- It is possible to prepare in a reproducible way formulations for which the flow and injectability properties are similar, starting with several batches of different CSS, themselves derived from chitosans from different batches in the <<medium>> molecular mass range.

Example 20—Injectability of Chitosan Succinimide Formulations and of Commercial Viscosupplements The force required for injecting different formulations based on succinimide chitosan and on commercial viscosupplements through needles for injection of different types and suitable for intra-articular injection, is measured at room temperature according to the method described earlier (Table 25). The sizes of the different types of needles are defined in Example 23.

TABLE 25

Force required for injecting the formulations through
needles for injection of various sizes (in Newtons)

| Formulation | | Type of needle (<< normal-walled >>) | | | |
|---|---|---|---|---|---|
| | | 21 G | 22 G | 25 G | 27 G |
| 017-008 | CSS 2% (sans GP) | 2.5 | / | 5 | 9 |
| 014-084 | CSS1%/HA 1% (sans GP) | | 4 | 8 | 13 |
| 016-008B | CSS 2% (avec GP) | / | / | / | 13 |
| VS1 | VS1 | 9 | / | / | 20 |
| VS2 | VS2 | 2.5 | / | / | 9 |
| VS3 | VS3 | 4 | 7 | 15 | Injectable with difficulty* |

*presence of pieces of gel

From this example it is understood that the formulations of gels based on chitosan succinimide are easily injectable through fine needles at room temperature, while having high flow characteristics at a physiological temperature of 37° C.

Example 21—Sensitivity to Degradation In Vitro Under Conditions of Oxidizing Stress In this example, formulations based on chitosan succinimide and on commercial viscosupplements are put under oxidizing stress conditions in vitro for simulating an inflammatory environment, according to a procedure adapted from the publication of Mendoza et al. (Carb Res 342, 96, 2007). The procedure consists of generating free hydroxyl radicals by Fenton's reaction between cupric ions and hydrogen peroxide, and of putting the gels in presence for 24 hours at a temperature of 37° C. The gels are sampled and their elastic modulus G' and their dynamic viscosity are measured for characterizing the impact of the incubation.

Briefly, 800 µg of a gel formulation based on CSS or on a commercial viscosupplement based on HA are placed in a test tube. 100 µg of an EDTA solution of a concentration of 220 µM and 70 µg of a solution of copper sulfate at a concentration of 1 mM are added. The mixture is homogenized and the mixture is left to incubate at 37° C. for 24 hours. 30 µg of a hydrogen peroxide solution 0.03 M are added and the solution is then sampled at different time intervals, and the flow properties are measured with the rheometer Discovery HR-2 (TA) at 37° C. according to the method described earlier.

The relative elastic modulus ($G'_R$) and the relative dynamic viscosity ($\eta_R$) are calculated according to the formulae 1 and 2, respectively:

$G'_R = G'$ at time $t/G'$ at time zero×100 (Table 26a)  Formula 1:

$\eta_R = \eta$ at time $t/\eta$ at time zero×100 (Table 26b)  Formula 2:

TABLE 26a

Relative elastic modulus ($G'_R$) of the gels at a frequency of 0.6
Hz (3.98 rad/s), versus the incubation time in an oxidizing medium

| Formulation (reference) | Type | 0 hr | 2 hr | 4 hr | 24 hr |
|---|---|---|---|---|---|
| 017-008 | Gel CSS (2%) | 100% | 127% | 125% | 92% |
| 014-084 | Gel CSS (1%)/HA (1%) | 100% | 99% | 42% | 51% |
| VS1 | Viscosupplement based on non-cross-linked HA | 100% | 45% | 9% | 14% |
| VS3 | Viscosupplement based on cross-linked HA | 100% | 78% | 11% | 10% |

TABLE 26b

Relative dynamic viscosity ($\eta_R$) of the gels
versus the incubation time in an oxidizing medium

| Formulation (reference) | 0 hr | 2 hr | 4 hr | 24 hr |
|---|---|---|---|---|
| 017-008 | 100% | 129% | 128% | 92% |
| 014-084 | 100% | 99% | 46% | 51% |
| VS1 | 100% | 51% | 22% | 13% |
| VS3 | 100% | 86% | 14% | 10% |

The gel formulations based on CSS of this example are significantly more resistant to degradation in an oxidizing medium than the commercial formulations based on cross-linked hyaluronic acid (VS2) or non-cross-linked hyaluronic acid (VS1), and they retain their capability of absorbing shocks (G') and their lubricating power (η) for a prolonged period, of at least 24 hours.

Example 22—Osmolality of Aqueous Solutions of Sodium Beta-Glycerophosphate 10 g of sodium beta-glycerophosphate are dissolved in 100 ml of osmosed water. The solution is stirred until total dissolution, and then diluted at different concentrations by adding water. The osmolality of the solutions is measured according to the method described earlier (Table 27).

TABLE 27

Osmolality of sodium beta-glycerophosphate
solutions (GP) in water

| GP concentration (g/100 ml) | Osmolality (mosmol/kg) |
|---|---|
| 2% | 155 |
| 4% | 296 |
| 6% | 438 |
| 7% | 512 |
| 8% | 590 |
| 9% | 658 |
| 10% | 745 |

Thus it is noted that the osmolality increases with the glycerophosphate concentration in such compositions. Thus, a composition comprising more than 10% of glycerophosphate has an osmolality ranging beyond the desired osmolality for the applications contemplated in the present invention.

In particular, the publications of YUHUA Chang et al., (<<Preparation and properties of a novel thermosensitive N-trimethyl chitosane hydrogel, Polymer Bulletin, Springer, Berlin, DE, 63, 531) and WU J. et al. (A thermo- and pH-sensitive hydrogel composed of quaternized chitosan/ glycerophosphate, International Journal of Phamarmaceutics, Elsevier, BV, NL, 315, No 1-2, pages 1-11) describe compositions comprising more than 10% by mass of glycerophosphate. The osmolality of these compositions is therefore greater than 700 mosmol/kg and much greater than 500 mosmol/kg.

It is possible to notably refer to the document relating to the health safety of the product Nuflexxa® (Savient Pharmaceuticals, Inc.; osmolality of 258-381 mosm/kg) and of Negoro et al. (Effect of osmolarity on glycosaminoglycan production and cell metabolism of articular chondrocyte under three-dimensional culture system, Clinical and Experimental Rheumatology 2008, 26, 534-541) for the importance of the osmolality range. An osmolality of about 400 mosm/kg is a therapeutically excellent value since it exerts a strong influence on the proliferation of cells such as chondrocytes, osteocytes and fibroblasts.

Example 23—Diameters of the Needles for Injection

The sizes of needles for injection are defined by the ISO9262:1991 and the amendment ISO9262:1991/Amd.1: 2001(E). The outer diameter is fixed with a tolerance in the value (min-max range), while the inner diameter of the needles depends on the thickness of the walls, which are of a normal thickness («normal-walled»), thin thickness («thin-walled») or extra-thin («extra-thin-walled») depending on the types of needle and on the applications. Table 28 repeats the outer diameters (min/max) and the minimum inner diameters of the types of needles commercially available.

TABLE 28

Range of needles of different thicknesses for injection and tolerance of the inner and outer diameters, according to the ISO9262: 1991/Amd.1: 2001 (E) standard.

| Type | Size | Outer diameter (µm) | | Inner diameter (µm) | | |
|---|---|---|---|---|---|---|
| | | | | «Normal-walled» or «Regular» | «Thin-walled» | «Extra-thin-walled» |
| (Gauge)* | (mm) | Min | Max | Min | Min | Min |
| 32 | 0.23 | 229 | 241 | 89 | 105 | / |
| 31 | 0.25 | 254 | 267 | 114 | 125 | / |
| 30 | 0.30 | 298 | 320 | 133 | 165 | / |
| 29 | 0.33 | 324 | 351 | 133 | 190 | / |
| 28 | 0.36 | 349 | 370 | 133 | 190 | / |
| 27 | 0.40 | 400 | 420 | 184 | 241 | / |
| 26 | 0.45 | 440 | 470 | 232 | 292 | / |
| 25 | 0.5 | 500 | 530 | 232 | 292 | / |
| 24 | 0.55 | 550 | 580 | 280 | 343 | / |
| 23 | 0.60 | 600 | 673 | 317 | 370 | 460 |
| 22 | 0.70 | 698 | 730 | 390 | 440 | 522 |
| 21 | 0.80 | 800 | 830 | 490 | 547 | 610 |
| 20 | 0.90 | 860 | 920 | 560 | 635 | 687 |
| 19 | 1.10 | 1030 | 1100 | 648 | 750 | 850 |
| 18 | 1.20 | 1200 | 1300 | 790 | 910 | 1041 |

*for information

Example 24—Recommendations on the Types of Needles for Injection

Table 29 lists the types of needles which are recommended for the injection of different commercial products for repair, treatment or filling, for example in an intra-articular route for different commercial viscosupplementation products, via an intra-dermal or sub-cutaneous route for commercial products for filling the dermis, via a surface intra-dermal route for commercial products with view to regenerating the skin, or further via an intra-camerular for ophthalmology. The outer and inner diameters of these types of needles are indicated in Example 23.

TABLE 29

Types of recommended needles for administration by injection, according to the site and to the type of injection and the relevant product

| Product | Type and site of injection | Recommended needle size |
|---|---|---|
| Intra-articular viscosupplement (VS1) | Intra-articular/Knee | 19 to 21 Gauge |
| Intra-articular viscosupplement (VS2) | Intra-articular/Knee | 20 Gauge |
| Intra-articular viscosupplement (VS3) | Intra-articular/Knee | 18 to 20 Gauge |
| Intra-articular viscosupplement (VS4) | Intra-articular/Fingers | 19 to 25 Gauge |
| Repairing the cartilage by arthroscopy* | Arthroscopy/Knee, hip | 18 Gauge |
| Wrinkle filling based on cross-linked hyaluronic acid | Intra-dermal/Face | 25 to 27 Gauge |
| Wrinkle filling based on bioresorbable microparticles | Intra-dermal/Face | 26 Gauge |
| Rejuvenation of the skin based on non-cross-linked hyaluronic acid | Sub-cutaneous or intra-dermal/Face, hands, neck | 30 to 32 Gauge** |
| Antibioprophylaxy | Intracamerular/Anterior chamber of the eye | 30 G |

*in: Stanish et al. 2006;
**for example a needle of the « pen needle » type Micro-Fine™ Ultra 4 mm (32 G) marketed by BD.

What is claimed is:

1. A thermogelling composition comprising a chitosan having N-acetyl-glucosamine units, glucosamine units, and substituted glucosamine units other than the N-acetyl-glucosamine units, said substituted chitosan having a degree of substitution of the glucosamine units ranging from 10 to 50%, expressed as a number of moles of the substituent based on the number of moles of total units, the composition having an osmolality from 100 to 700 mosm/kg.

2. The thermogelling composition of claim 1, wherein the composition has a thermoreversible sol-gel transition.

3. The thermogelling composition of claim 1, wherein the composition has an osmolality from 200 to 500 mosm/kg.

4. The thermogelling composition of claim 1, wherein the chitosan concentration is less than 4% by mass based on the total mass of the composition (m/m).

5. The thermogelling composition of claim 1, wherein the composition comprises a gelling agent.

6. The thermogelling composition of claim 1, wherein the composition has a pH greater than or equal to 7.

7. The thermogelling composition of claim 1, wherein the composition has a pH from 7.2 to 8.5.

8. The thermogelling composition of claim 1, wherein the composition does not comprise any glycerol salt.

9. The thermogelling composition of claim 1, wherein the composition has in the fluid state a viscosity from 20 to 800 mPa·s.

10. The thermogelling composition of claim 1, wherein the composition has in the fluid state a viscosity from 40 to 500 mPa·s.

11. The thermogelling composition of claim 1, wherein the composition comprises a buffer.

12. The thermogelling composition of claim 1, wherein the composition comprises an acetate buffer.

13. The thermogelling composition of claim 1, wherein the composition comprises a reducing sugar.

14. The thermogelling composition of claim 1, wherein the composition comprises D-mannitol.

15. An injectable composition comprising or consisting of the thermogelling composition of claim 1.

16. A pharmaceutical composition or medical device comprising or consisting of the injectable composition of claim 15.

17. A method for treating arthrosis, or repairing a cartilage defect, the method comprising injecting the pharmaceutical composition or medical device of claim 16.

18. A method for preparing a thermogelling composition comprising a substituted chitosan having N-acetyl-glucosamine units, glucosamine units, and substituted glucosamine units other than the N-acetyl-glucosamine units, the composition having an osmolality from 100 to 700 mosm/kg; the method comprising:
    dissolving the substituted chitosan in an aqueous solution, optionally buffered, preferably at a pH comprised between 6.2 and 8.5;
    optionally adjusting the pH to a physiological pH;
    optionally adjusting the osmolality of the composition; and
    optionally adjusting the viscosity of the composition.

19. The method of claim 17, wherein said method comprises the injection of said pharmaceutical composition or medical device via intra-articular route.

20. The method of claim 17, wherein said method comprises the injection of said pharmaceutical composition or medical device into one or more cartilage, joint, or combination thereof, for repairing or filling said cartilage, joint or combination thereof.

21. The method of claim 17, wherein said method comprises the injection of said pharmaceutical composition or medical device into an articular joint for repairing or filling said articular joint.

22. The method of claim 17, wherein said method comprises the intra-articular injection of said pharmaceutical composition or medical device into one or more joint selected from the group consisting of a knee joint, a finger joint, and a hip joint.

23. The method of claim 17, wherein said method comprises the injection of said pharmaceutical composition or medical device into a synovial fluid of a human being affected with osteo-arthrosis.

24. The method of claim 17, wherein said method comprises the injection of said pharmaceutical composition or medical device into a synovial fluid from the knee of a human being affected with osteo-arthrosis.

25. A method of esthetical care or treatment method by dermal filling, said method comprising the injection into a human or animal body of a thermogelling composition comprising a chitosan having N-acetyl-glucosamine units, glucosamine units, and substituted glucosamine units other than the N-acetyl-glucosamine units, said substituted chitosan having a degree of substitution of the glucosamine units ranging from 10 to 50%, expressed as a number of moles of the substituent based on the number of moles of total units, the composition having an osmolality from 100 to 700 mosm/kg of claim 16 into a dermis.

26. The method of claim 25, wherein said method comprises the injection of said composition via a sub-cutaneous or intra-dermal route.

27. The method of claim 25, wherein said method is a surface treatment method for the skin by multiple injection via an intra-dermal route.

28. The method of claim 25, wherein said method comprises re-inflating skin so as to have it loose its crumpled appearance or for the treatment of wrinkles or lines.

29. The method of claim 25, wherein said method is for the skin rejuvenation by multiple injection via an intra-dermal route.

30. A dermatology composition or medical device comprising or consisting of the injectable composition of claim 15.

31. A mixture of a pharmaceutical composition or medical device of claim 16 and a synovial fluid.

32. A method of therapeutic treatment, wherein said method comprises the injection into a human or animal body of a pharmaceutical composition or medical device of claim 16 via intra-ocular route for repairing or filling an ocular tissue.

33. The thermogelling composition of claim 5, wherein said gelling agent is a glycerol phosphate salt.

34. The thermogelling composition of claim 5, wherein said gelling agent is present in the composition at a concentration comprised between 1 and 20% by mass based on the total mass of the final composition (m/m).

35. A method of delivery of at least one therapeutic agent, said method comprising injecting into a human or animal body a thermogelling composition of claim 1 as a therapeutic vector for targeted delivery and/or controlled release of at least one therapeutic agent contained in said thermogelling composition.

* * * * *